United States Patent
Isaka et al.

(10) Patent No.: US 10,288,581 B2
(45) Date of Patent: May 14, 2019

(54) GAS SENSOR MANUFACTURING METHOD AND GAS SENSOR MANUFACTURING APPARATUS

(71) Applicant: NGK INSULATORS, LTD., Nagoya (JP)

(72) Inventors: Kenji Isaka, Nagoya (JP); Nobukazu Ikoma, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 227 days.

(21) Appl. No.: 15/464,710

(22) Filed: Mar. 21, 2017

(65) Prior Publication Data

US 2017/0276637 A1 Sep. 28, 2017

(30) Foreign Application Priority Data

Mar. 25, 2016 (JP) .................. 2016-061511

(51) Int. Cl.
*G01N 27/407* (2006.01)
*G01N 33/00* (2006.01)

(52) U.S. Cl.
CPC ..... *G01N 27/4078* (2013.01); *G01N 33/0037* (2013.01); *Y10T 29/49829* (2015.01); *Y10T 29/49934* (2015.01); *Y10T 29/53187* (2015.01)

(58) Field of Classification Search
CPC ............. G01N 27/4062; G01N 27/407; G01N 27/4078; G01N 27/409; G01N 33/0009;
(Continued)

(56) References Cited

U.S. PATENT DOCUMENTS 9,188,576 B2 * 11/2015 Hirata ................ G01N 33/0009
9,335,312 B2 * 5/2016 Kato .................. G01N 27/4078
(Continued)

FOREIGN PATENT DOCUMENTS

EP 2 784 498 A1 10/2014
EP 3 093 655 A1 11/2016
(Continued)

OTHER PUBLICATIONS

U.S. Appl. No. 15/464,740, filed Mar. 21, 2017, Kenji Isaka.
Extended European Search Report (Application No. 17162908.2) dated Jul. 21, 2017.

*Primary Examiner* — Peter Dungba Vo
*Assistant Examiner* — Joshua D Anderson
(74) *Attorney, Agent, or Firm* — Burr & Brown, PLLC

(57) ABSTRACT

Provided is a method for manufacturing a gas sensor capable of securing airtightness without a chip in a sensor element. The method includes a step of obtaining an assembled body constituting the gas sensor, including steps of: causing one end of the sensor element to abut to a positioning member for positioning the sensor element; applying a force F1 to the annularly-mounted members including a powder compact annularly mounted to the sensor element under a state that the sensor element is positioned and thereby compressing the powder compact so as to fix the sensor element inside of the tubular body, applying a force F2 larger than the force F1 to the annularly-mounted members under a state that the sensor element is not positioned and thereby further compressing the powder compact, so as to hermetically seal inside of the tubular body.

17 Claims, 30 Drawing Sheets

(58) Field of Classification Search
CPC .......... G01N 33/0037; Y10T 29/49002; Y10T 29/49007; Y10T 29/49126; Y10T 29/49826; Y10T 29/49828; Y10T 29/49829; Y10T 29/49934; Y10T 29/5313; Y10T 29/53178; Y10T 29/53265
USPC ............. 73/23.2, 23.31, 31.05; 204/424–431
See application file for complete search history.

(56) References Cited

U.S. PATENT DOCUMENTS

| | | | |
|---|---|---|---|
| 9,423,368 B2 * | 8/2016 | Makino | ................... G01N 27/12 |
| 2005/0022361 A1 | 2/2005 | Matsuo et al. | |
| 2015/0253298 A1 | 9/2015 | Isaka et al. | |
| 2016/0273944 A1 * | 9/2016 | Hattori | ............... G01N 27/4078 |
| 2018/0281331 A1 * | 10/2018 | Isaka | ......................... B30B 9/00 |

FOREIGN PATENT DOCUMENTS

| | | |
|---|---|---|
| JP | 2008-145339 A1 | 6/2008 |
| JP | 2015-169606 A1 | 9/2015 |

* cited by examiner

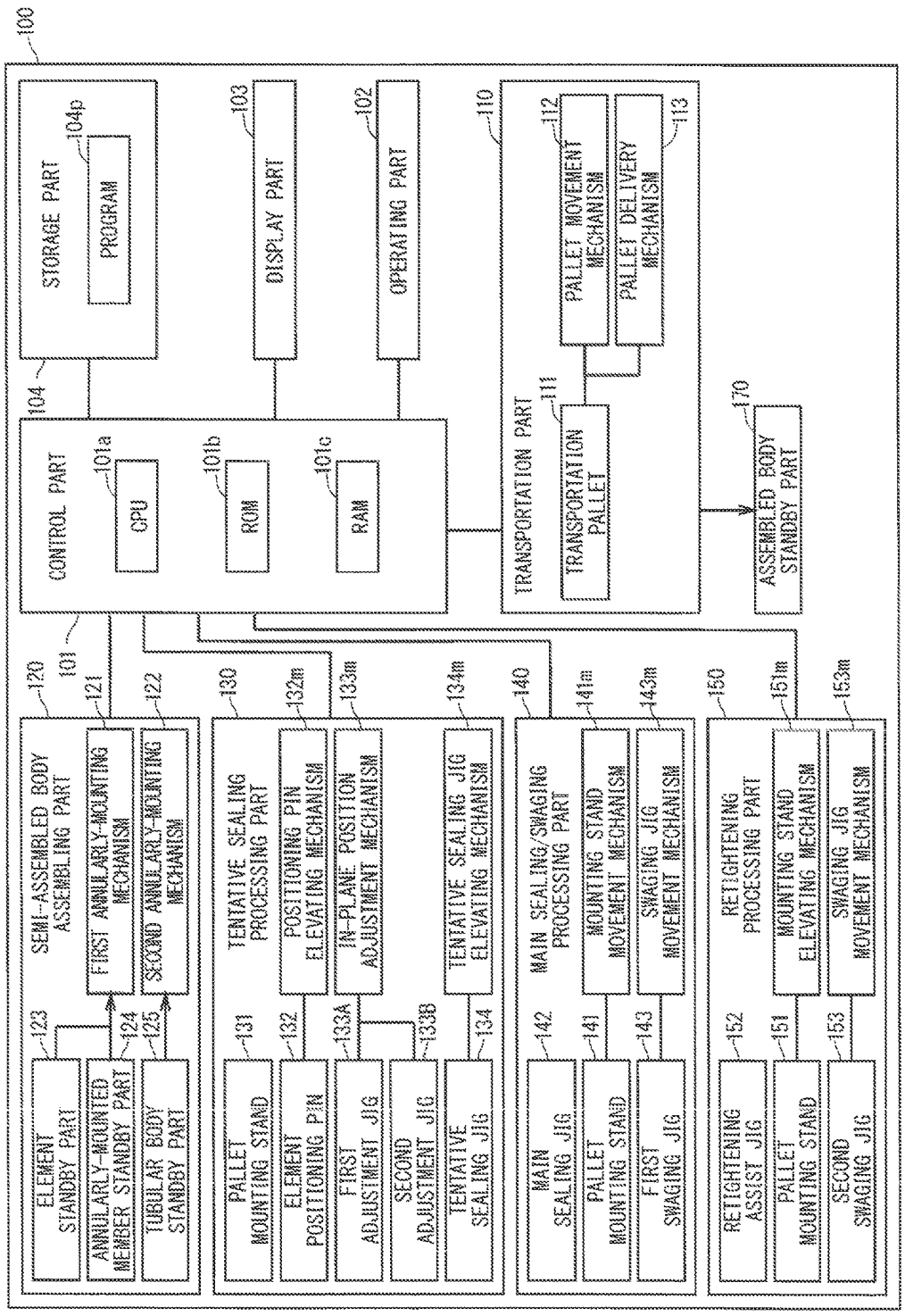
F I G. 4

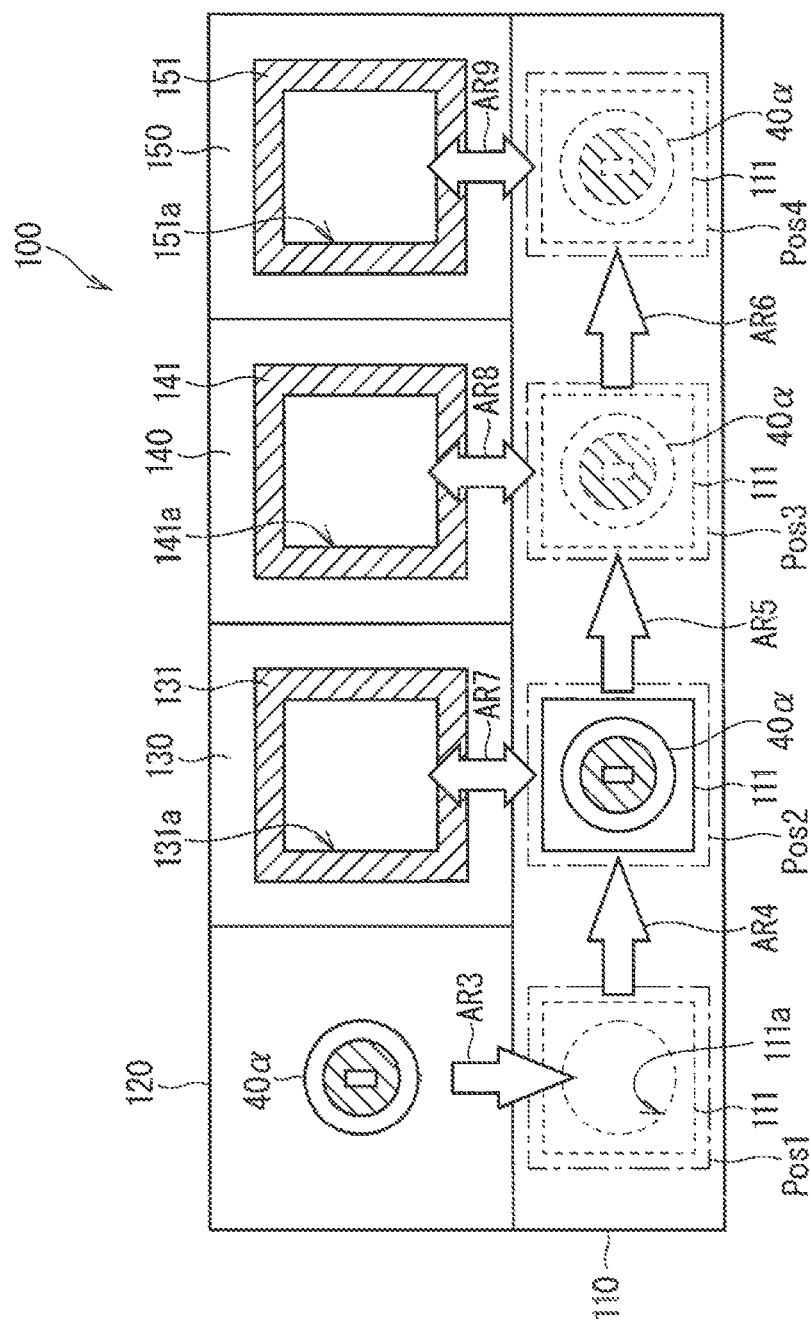

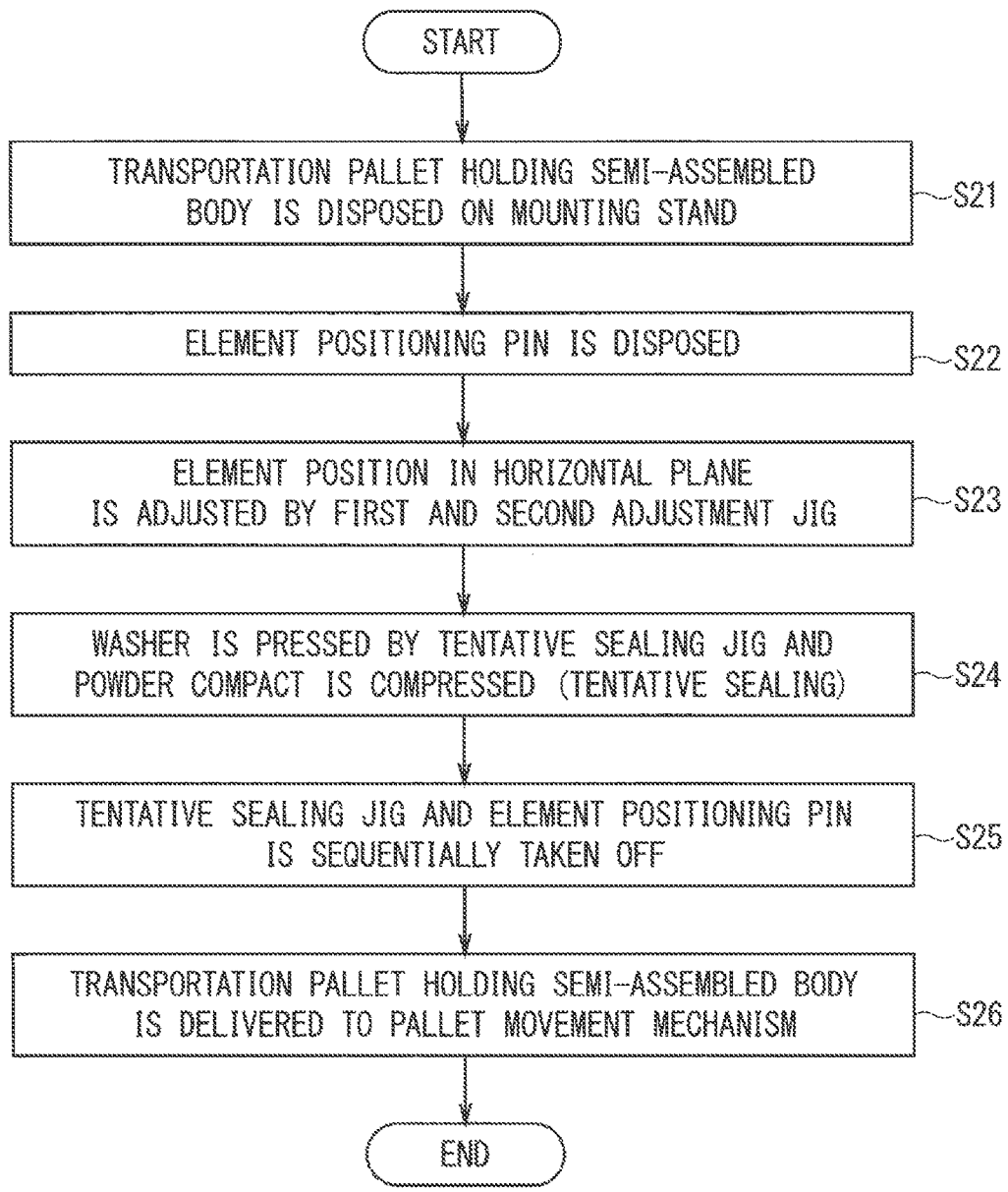

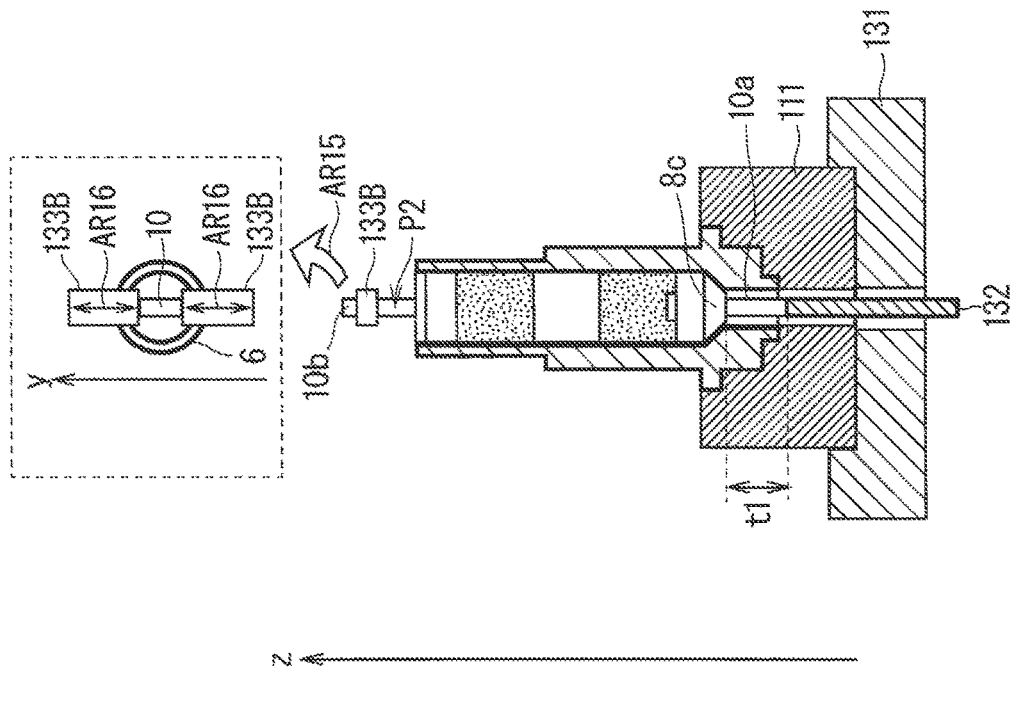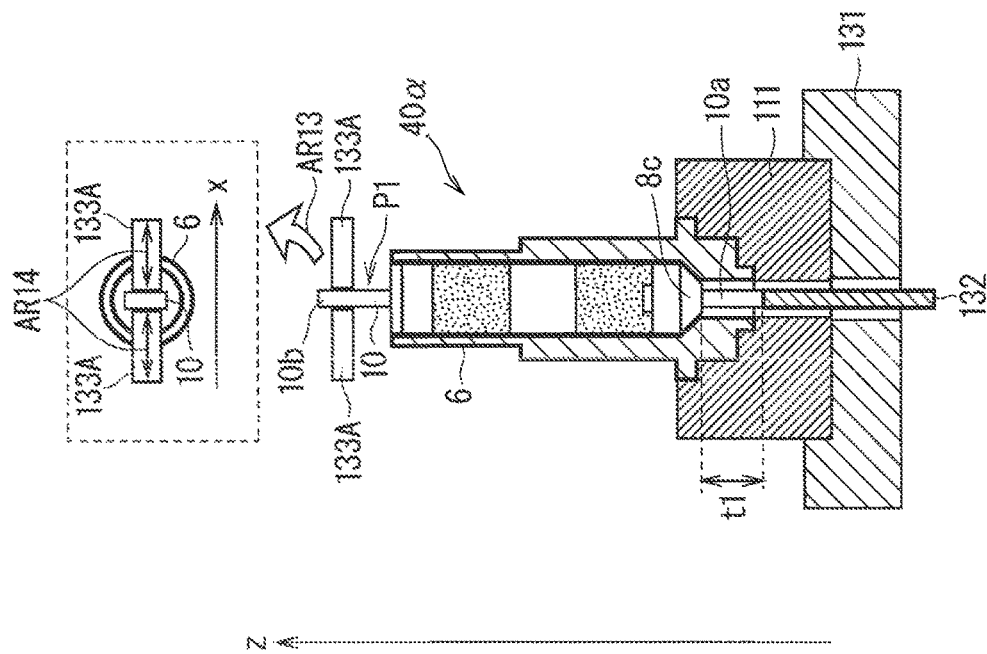

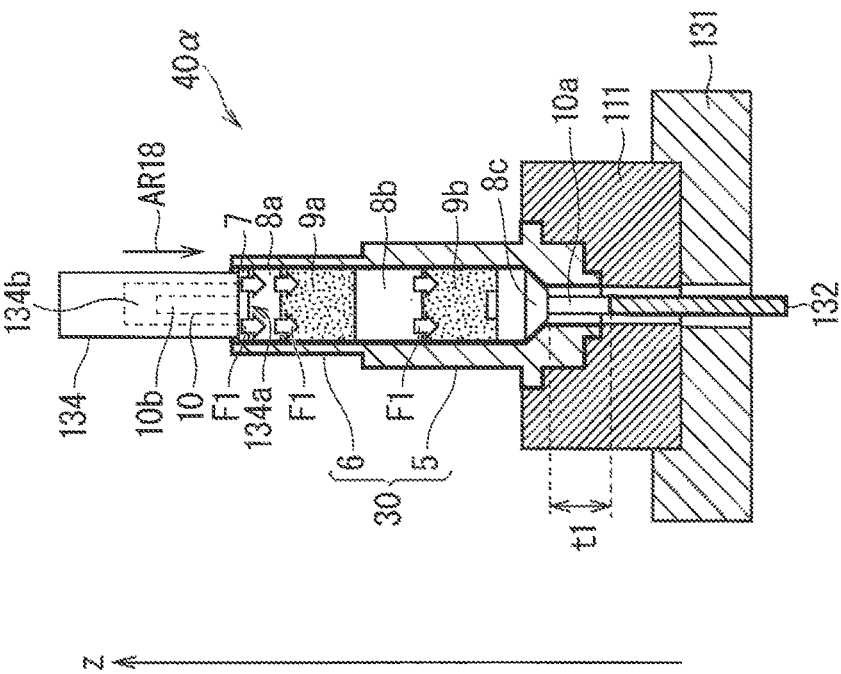
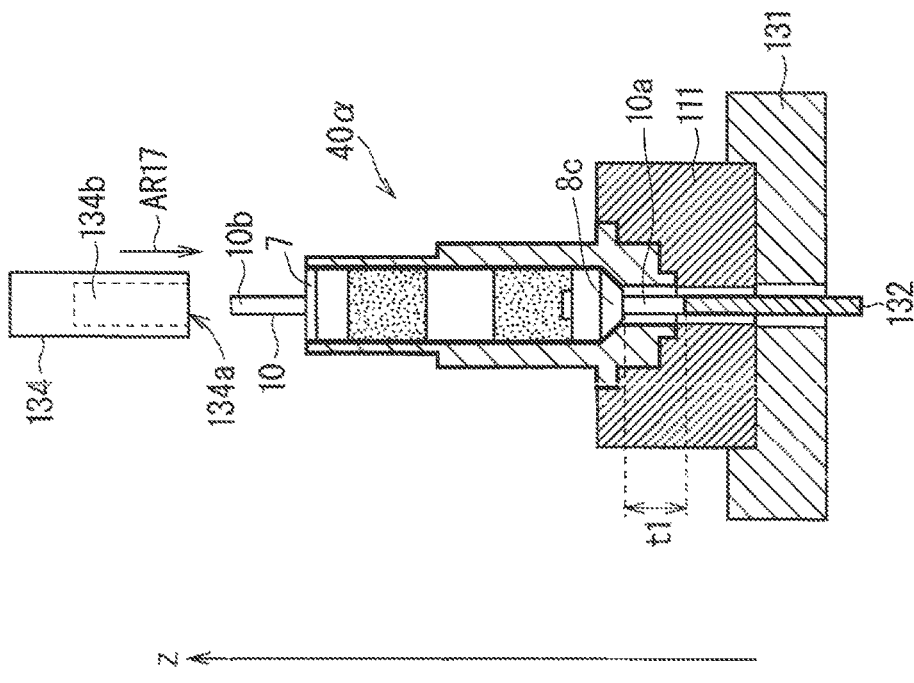

FIG. 19
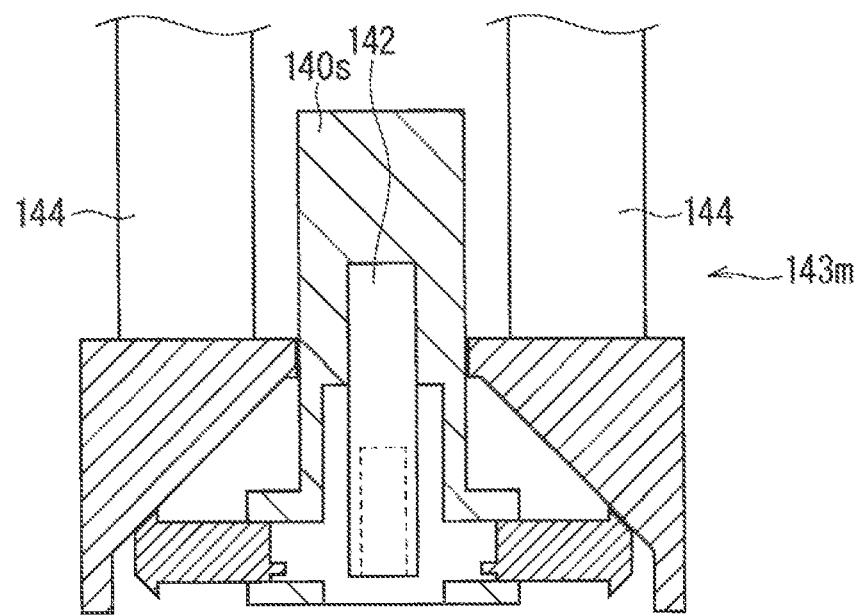
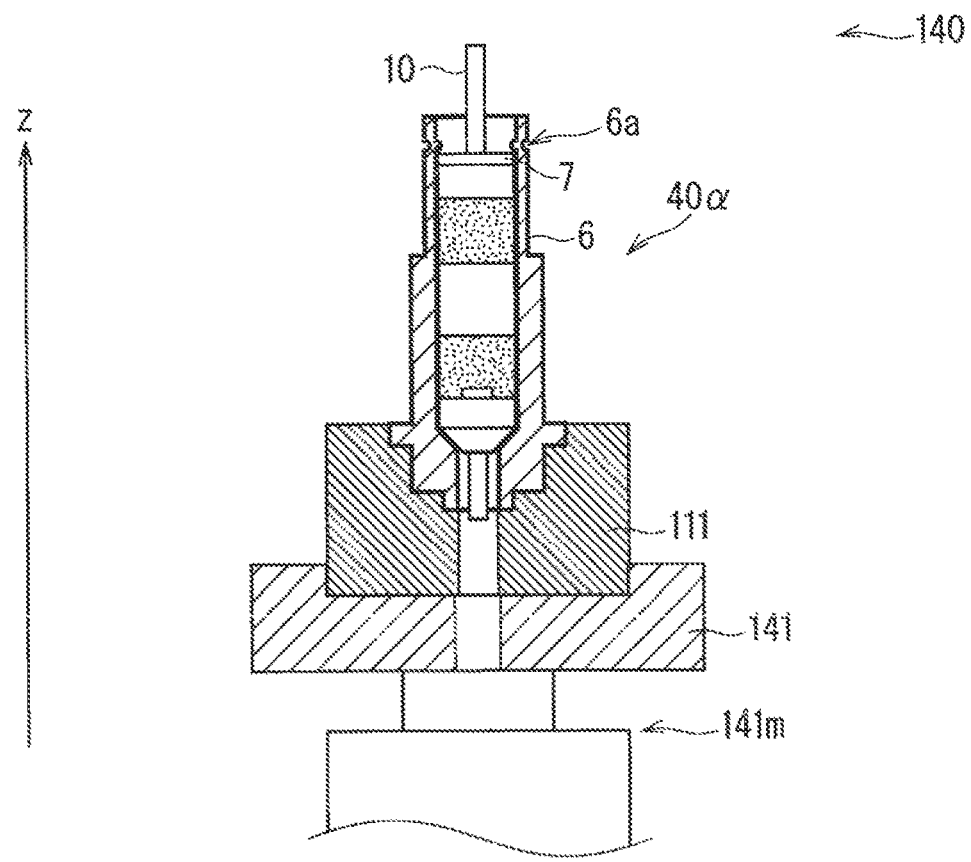

F I G. 2 4
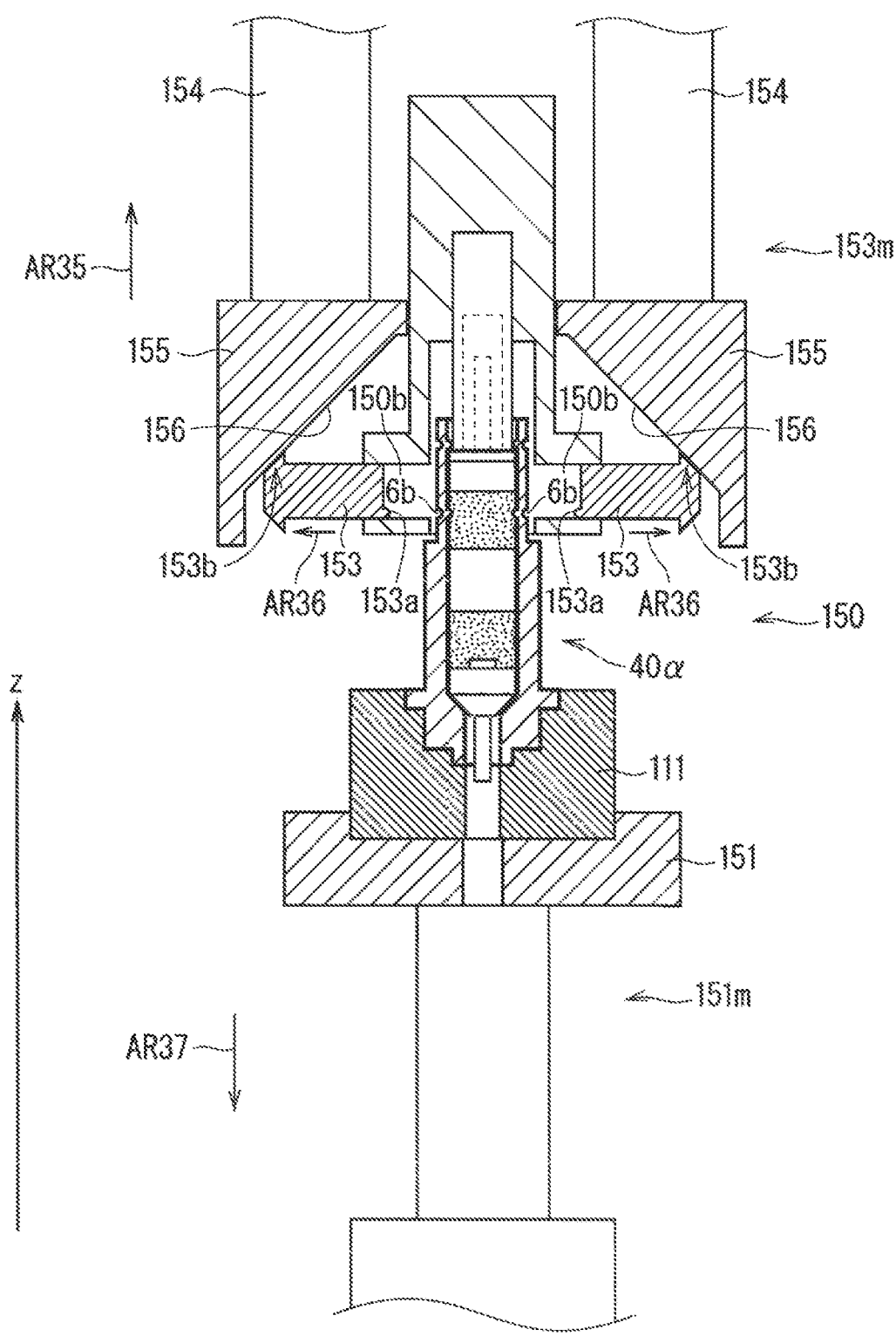

FIG. 25
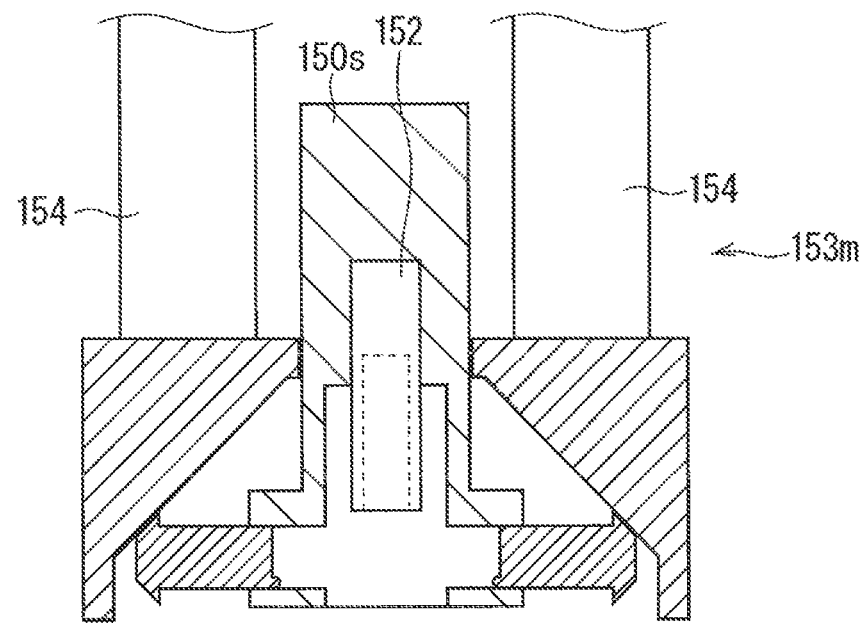
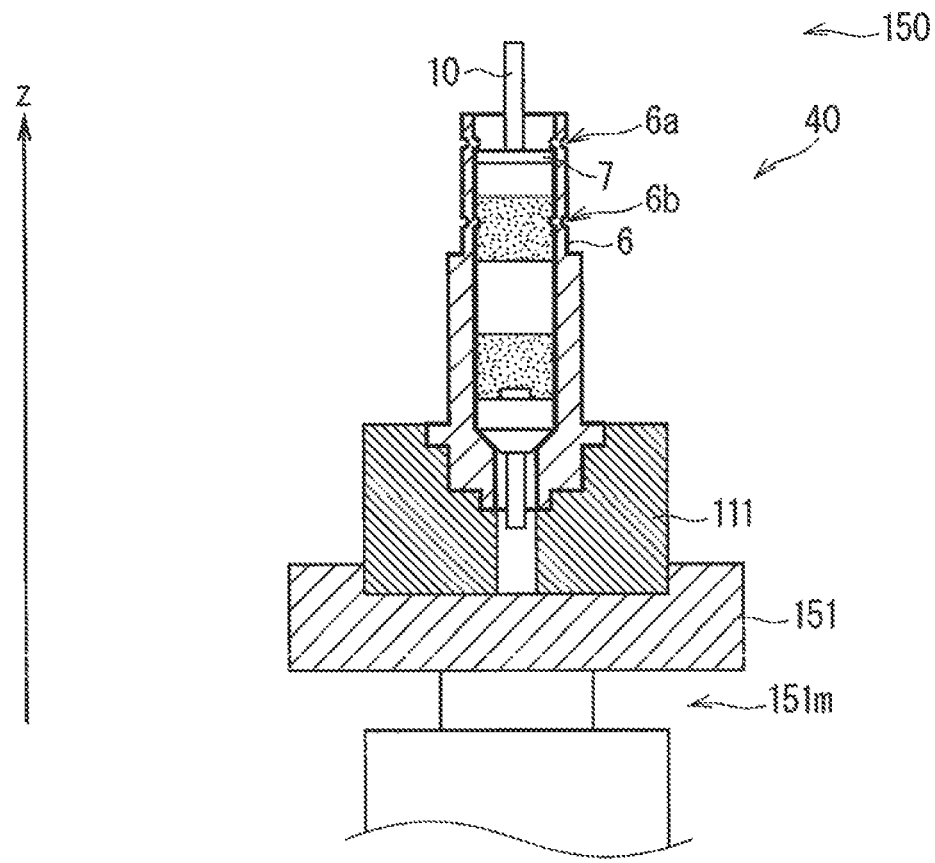

F I G. 3 0
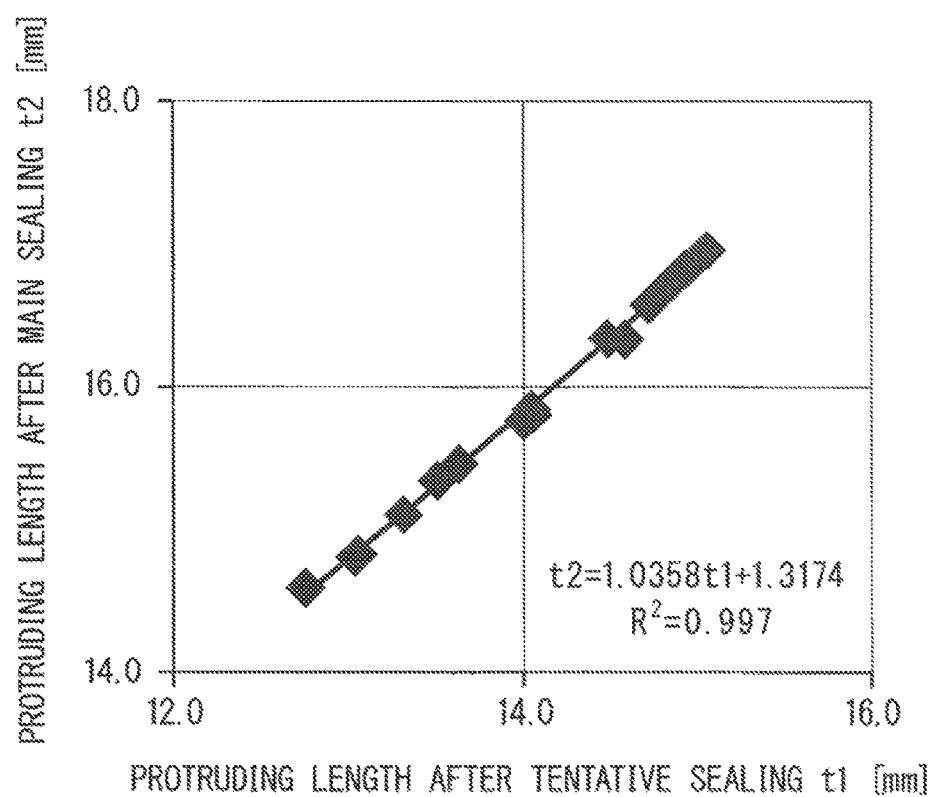

GAS SENSOR MANUFACTURING METHOD AND GAS SENSOR MANUFACTURING APPARATUS

BACKGROUND OF THE INVENTION

Field of the Invention

The present invention relates to a method for manufacturing a gas sensor including a ceramic sensor element.

Description of the Background Art

Conventionally, there have been well known gas sensors having sensor elements formed from an oxygen-ion conductive solid electrolyte ceramic, such as zirconia ($ZrO_2$), as devices for determining the concentrations of predetermined gas components in measurement gas, such as combustion gasses and exhaust gasses in internal combustion engines such as automobile engines.

Such gas sensors generally include a sensor element (detection element) with an elongated plate shape which is made of a ceramic, wherein the sensor element is secured by a plurality of ceramic supporters which are ceramic insulators and by powder compacts made of ceramics such as talc which are embedded between the ceramic supporters, in a hollow portion of a metal housing and a cylindrical inner tube secured thereto through welding so that the powder compacts provide hermetic sealing between a space, on one end side of the sensor element and a space on the other end side of the sensor element. The hermetic sealing is achieved by pressing the ceramic supporters and the powder compacts which are sequentially and annularly mounted to the sensor element using a predetermined sealing jig to compress the powder compacts, and subsequently swaging the inner tube from outside using a predetermined swaging jig (refer to Japanese Patent Application Laid-Open No. 2015-169606, for example).

In order to secure airtightness with the hermetic sealing described above, a pressing by a sealing needs to be performed with a relatively high load of 400 kgf or more, for example. In addition, the sensor element needs to be disposed in a correct position in a correct attitude after the hermetic sealing so that the gas sensor satisfies a desired characteristics.

If the sensor element is inclined and comes in contact with the ceramic supporters at the time of the sealing, thereby being subjected to an action of a stress from the ceramic supporters, a crack may occur in a portion of the sensor element being in contact with the ceramic supporters in a process of manufacture or in use, or the sensor element may be broken at the contact portion. In a manufacturing process, it is required that a generation of such a defective product is reduced and, if the defective product is generated, it needs to be reliably found and excluded from a shipping object.

SUMMARY OF THE INVENTION

The present invention relates to a method for manufacturing a gas sensor including a ceramic sensor element and, more particularly, is directed to a hermetic sealing at a time of fixing the sensor element in the gas sensor.

According to the present invention, the method for manufacturing the gas sensor, the method including a step of obtaining an assembled body constituting the gas sensor by performing a predetermined processing on a semi-assembled body which is manufactured in advance, and the semi-assembled body includes: an annular-mounted assembly in which a plurality of annularly-mounted members, at least one of which is a ceramic powder compact, each having a disc shape or cylindrical shape are annularly mounted to a sensor element with an elongated plate shape which is mainly made of a ceramic; and a tubular body which is annularly mounted to an outer periphery, of the annularly-mounted members and capable of engaging one end side of the annularly-mounted members therein. The step of obtaining the assembled body includes steps of: a) causing one end of the sensor element constituting the semi-assembled body to abut to a predetermined positioning member for positioning the sensor element; b) applying a first force to the annularly-mounted members from other end side of the sensor element having been positioned through the step a) and thereby compressing the powder compact so as to fix the sensor element inside of the tubular body; and c) after the step b), applying a second force which is larger than the first force to the annularly-mounted members from the other end side of the sensor element with the one end of the sensor element not abutting to the positioning member and thereby further compressing the powder compact so as to hermetically seal between spaces located on one end side and the other end side of the sensor element inside of the, tubular body.

According to the present invention, the second compression for the hermetic sealing between the spaces located on one end side and the other end side of the sensor element inside of the tubular body is successively performed subsequent to the first compression performed mainly for purpose of positioning the sensor element, without using the element positioning member, so that the hermetical sealing can be achieved without a chip or break in the sensor element.

Accordingly, an object of the present invention is to provide a method for manufacturing a gas sensor which suppresses a generation of a defective product caused by an improper posture of a sensor element inside the gas sensor.

BRIEF DESCRIPTION OF THE DRAWINGS

FIG. 4 is a block diagram schematically illustrating a structure of a manufacturing apparatus 100.

FIG. 6 is a planar view schematically illustrating a transport of a semi-assembled body 40α and the assembled body 40 in a transportation part 110 and a delivery of the semi-assembled body 40α between the transportation part 110 and respective parts.

FIG. 7 is a view illustrating a more specific procedure of a tentative sealing process.

FIGS. 9A and 9B are views illustrating a state halfway through the tentative sealing process in stages.

FIGS. 10A and 10B are views illustrating a state halfway through the tentative sealing process in stages.

FIG. 19 is a view illustrating a state halfway through the first swaging process in stages.

FIG. 24 is a view illustrating a state halfway through the second swaging process in stages.

FIG. 25 is a view illustrating a state halfway through the second swaging process in stages.

FIG. 30 is a view plotting a protruding length t2 after the main sealing with respect to a protruding length t1 at the time of the tentative sealing.

DESCRIPTION OF THE PREFERRED EMBODIMENTS

<Configuration of Gas Sensor>

Figure 1:
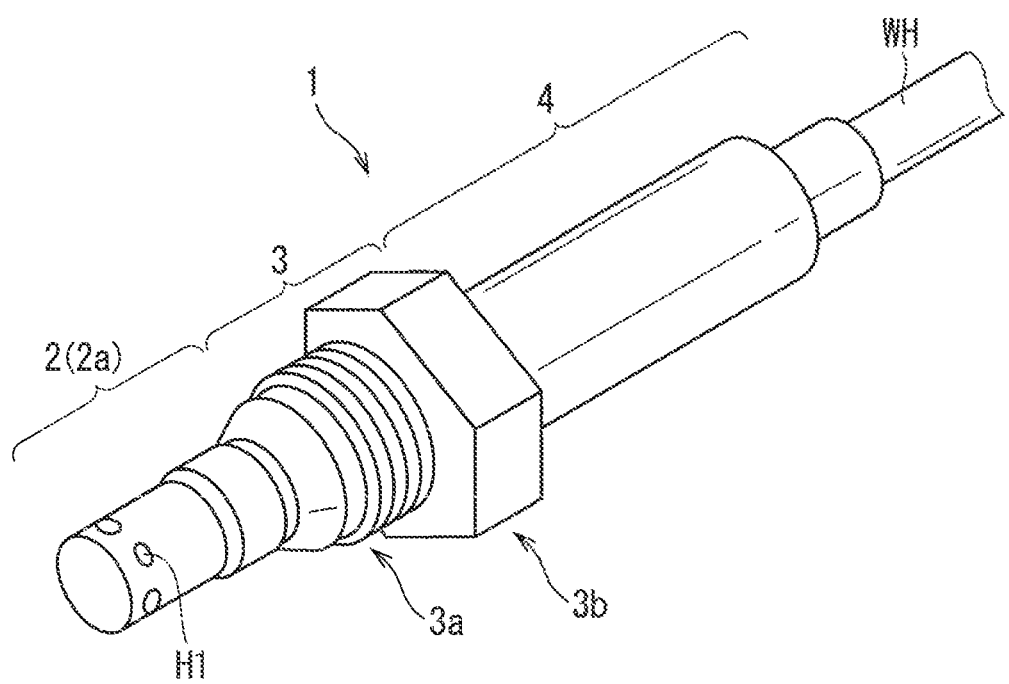
FIG. 1 is a perspective view of an external appearance of a gas sensor 1.
Figure 2:
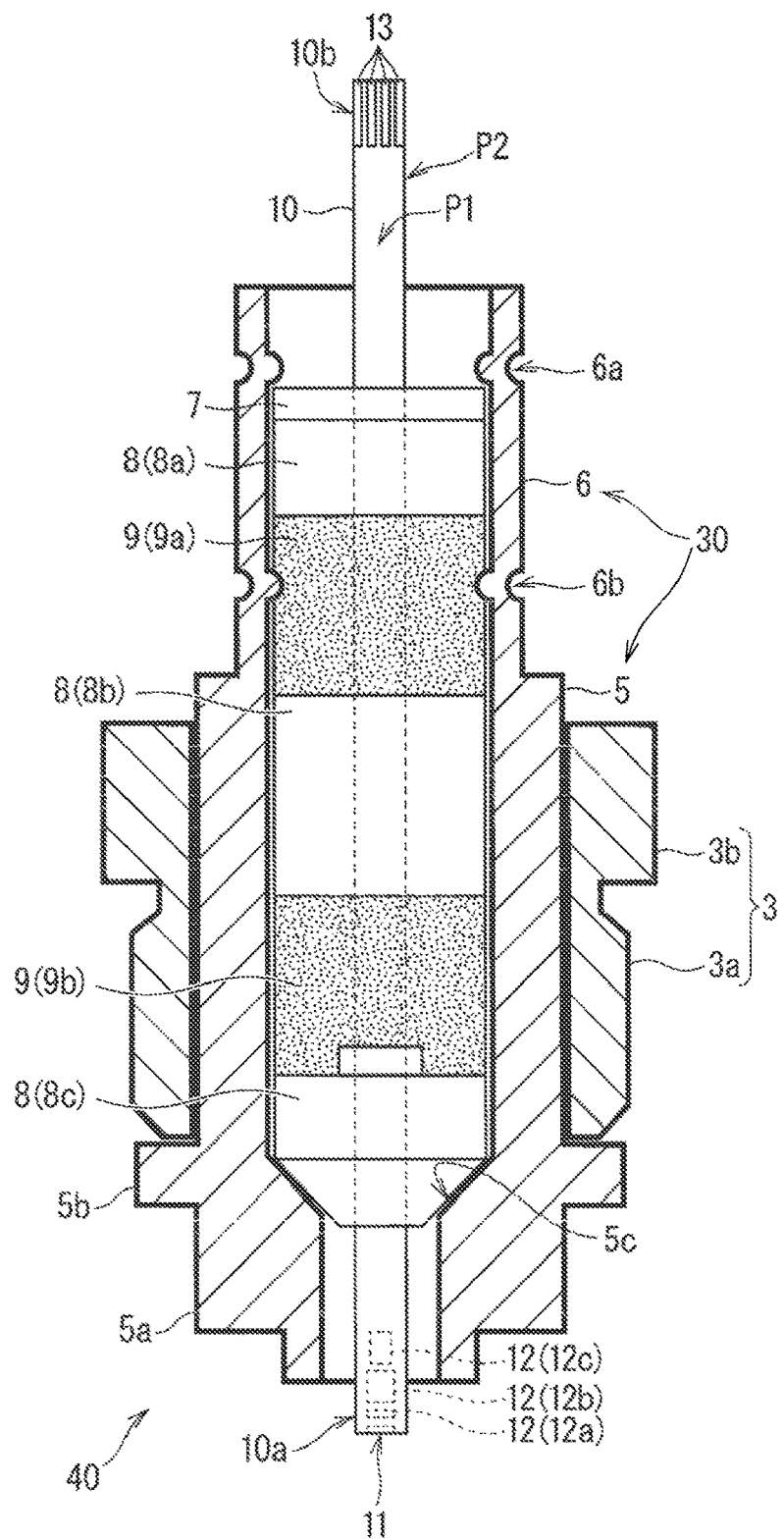
FIG. 2 is, a partial cross-sectional view illustrating a main structure inside the gas sensor 1.

FIG. 1 is an external perspective view of a gas sensor (more specifically, a main body thereof) 1 to be assembled in this preferred embodiment. FIG. 2 is a partial cross-sectional view illustrating a main structure inside the gas sensor 1. In this preferred embodiment, the gas sensor 1 serves to detect, a predetermined gas component (such as NOx) with a sensor element 10 (FIG. 2) included therein.

The sensor element 10 is an elongated columnar or thin-plate like member including, as a main constituent material, an oxygen-ion conductive solid electrolyte ceramic such as zirconia. The sensor element 10 has a configuration in which a as inlet, an internal space, and the like are provided on a first tip portion 10a side and various electrodes and wiring patterns are provided on a surface and inside of an element body. In the sensor element 10, a detection gas introduced into the internal space is reduced or decomposed in the internal space, to thereby generate oxygen ions. The gas sensor 1 determines the concentration of the gas component based on a fact that an amount of oxygen ions flowing inside an element is proportional to the concentration of the gas component in the detection gas. A surface facing a front in FIG. 2 is referred to as a main surface P1 of the sensor element 10, and a surface that is perpendicular to the main surface P1 and extends along a longitudinal direction is referred to as a side surface P2. Both the main surface P1 and the side surface P2 extend in the longitudinal direction of the sensor element 10, and a width of the main surface P1 is larger than that of the side surface P2.

The outside of the gas sensor 1 is mainly formed of a first cover 2, a fixing bolt 3, and a second cover 4.

The first cover 2 is an approximately cylindrical exterior member that protects a portion of the sensor element 10 that comes in direct contact with the detection gas in use, which is specifically the first tip portion 10a including a gas inlet 11 and a closed space 12 (buffer space 12a, first internal space 12b, and second internal space 12c) and the like. The gas inlet 11 is open at the first tip portion 10a, which is the lowermost end of the sensor element 10 in FIG. 2. Each of the buffer space 12a, first internal space 12b, and second internal space 12c is provided inside the sensor element 10. The gas inlet 11, the buffer space 12a, the first internal space 12b, and the second internal space 12c are arranged in this order along the longitudinal direction of the sensor element 10 and are communicated with each other via a diffusion-controlling part.

More specifically, the first cover 2 has a double-layer structure of an outside cover 2a and an inside cover (not shown). Each of the outside cover 2a and inside cover has a circular bottom on one side and has a plurality of through holes through which a gas passes in the side portion. FIG. 1 illustrates through holes H1 provided in the outside cover 2a, which are merely an example. A position and number of through holes arranged may be appropriately determined in consideration of how a measurement gas flows into the first cover 2.

The fixing bolt 3 is an annular member to be used hen the gas sensor 1 is taxed at a measurement position. The fixing bolt 3 includes a threaded bolt portion 3a and a held portion 3b to be held when the bolt portion 3a is screwed. The bolt portion 3a is screwed with a nut provided at a position at which the gas sensor 1 is mounted. For example, the bolt portion 3a is screwed with a nut, portion provided in the car exhaust pipe, whereby the gas sensor 1 is fixed to the exhaust pipe such that the first cover 2 side thereof is exposed in the exhaust pipe.

The second cover 4 is a cylindrical member that protects other part of the gas sensor 1. A wire harness WH which houses a plurality of lead wires (not shown) for electrically connecting the gas sensor 1 and a drive controller (not shown) extends from an end of the second cover 4.

FIG. 2 shows the internal configuration of the gas sensor 1, more specifically, the configuration of the as sensor 1 except for the first cover 2 and second cover 4 shown in FIG. 1.

As shown in FIG. 2, inside the gas sensor 1, a washer 7, three ceramic supporters 8 (8a, 8b, and 8c), and two powder compacts 9 (9a and 9b) are each annularly mounted to the part of the sensor element 10 except for the first tip portion 10a, which includes the gas inlet 11 and the like, and a second tip portion 10b, which includes, a connection terminal (electrode terminal) 13 for connection with the lead wires (not shown) housed in the wire harness WH, such that the sensor element 10 is positioned about the axis. The ceramic supporter 8 is a ceramic insulator. Meanwhile, the powder compact 9 is obtained by shaping ceramic powders such as talc. In the following description, the washer 7, the ceramic supporters 8, and the powder compacts 9 are collectively referred to as annularly-mounted members, in some cases, and an assembly in a state that these annularly-mounted members are annularly mounted to the sensor element 10 is referred to, as a post-annularly-mounted assembly 31 (refer to FIGS. 5A to 5C), in some cases.

As shown in FIG. 2, a cylindrical tubular body (inner tube welded product) 30, which is obtained by integrating a housing 5 being a metallic cylindrical member and an inner tube 6 being a metallic cylindrical member, is annularly mounted to the outer peripheries of the washer 7, the ceramic supporters 8 (8a, 8b and 8c), and the power compacts 9 (9a and 9b).

The tubular body 30 is a member that the housing 5 and the inner tube 6 are integrated, with one end of the inner tube 6 welded to the housing 5. The housing 5 and the inner tube 6 have substantially the same inside diameter and are connected coaxially. An inside diameter of the tubular body 30 is set, to be larger than designed values of maximum outside diameters of the respective annularly-mounted members.

The housing 5 is provided with a tapered portion 5c at one end side of the inside thereof. One end side, of the post-annularly-mounted assembly 31 is engaged with an inside of the tubular body 30 by the tapered portion 5c. In a position of the inner tube 6 right above the washer 7 and a position of the inner tube 6 at the side of the powder compact 9a, respectively, concave portions 6a and 6b concaved inwardly are formed. Other end sides of the post-annularly-mounted assembly 31 are engaged with the inside of the tubular body 30 by the concave portions 6a and 6b.

More specifically, the powder compact 9 is compressed after being annularly mounted, and is thereby attached firmly to the sensor element 10. The concave portions 6a and 6b are provided after compressing the powder compact 9. As a result that the firm attachment of the powder compact 9 to the sensor element 10 is achieved, in the tubular body 30, the sensor element 10 is fixed, and a sealing is achieved between the first tip portion 10a side including the gas inlet 11 or the like and the second tip portion 10b including the connection terminal (electrode terminal) 13 for the connection with the lead wires or the like in the sensor element 10. According to the above configuration, airtightness between a measurement gas space including the inspected gas (the measurement gas) which the first tip portion 10a of the sensor element 10 contacts and a reference gas space including a reference gas such as the atmosphere, for example, which the second tip portion 10b contacts is secured. The concave portions 6a and 6b are provided to maintain the compression state of the powder compact 9.

In this preferred embodiment, the sealing (the hermetic sealing) for maintaining the airtightness is performed in two stages, that is, a tentative sealing (a first compression) and a main sealing (a second compression). The detail of the hermetic sealing is described hereinafter.

In the following description, referred to as the assembled body 40 is a configuration that the tubular body 30 is annularly mounted to the post-annularly-mounted assembly 31 and the concave portions 6a and 6b are provided in the post-annularly-mounted assembly 31 as shown in FIG. 2. In the meanwhile, a workpiece under a state that the formation of the concave portion 6b, which is last performed in sequential assembling processes, is not completed is referred to as a semi-assembled body 40α (refer to FIGS. 5A to 5C).

The assembled body 40 having the aforementioned configuration in FIG. 2 is covered with the first cover 2, fixing bolt 3, and second cover 4, finally to, form the gas sensor 1. Specifically, the first cover 2 is connected to a tubular portion 5a at a tip portion of the housing 5. The fixing bolt 3 is annularly mounted to the outer periphery of the housing 5 so as to come contact with a projection (a flange portion) 5b. Moreover, the second cover 4 is mounted so as to be fitted into an annular groove (not shown) between the fixing bolt 3 and housing 5, which is formed through the above annular mounting.

Due to the above-mentioned configuration, in the gas sensor 1, the atmosphere around the first tip portion 10a of the sensor element 10 (atmosphere in the first cover 2) is completely cut off from the outside atmosphere in a case that the gas sensor 1 is mounted at a predetermined position. This allows for accurate measurement of the concentration of a target gas component in the detection gas.

<Outline of Manufacture of Assembled Body>

Figure 3:
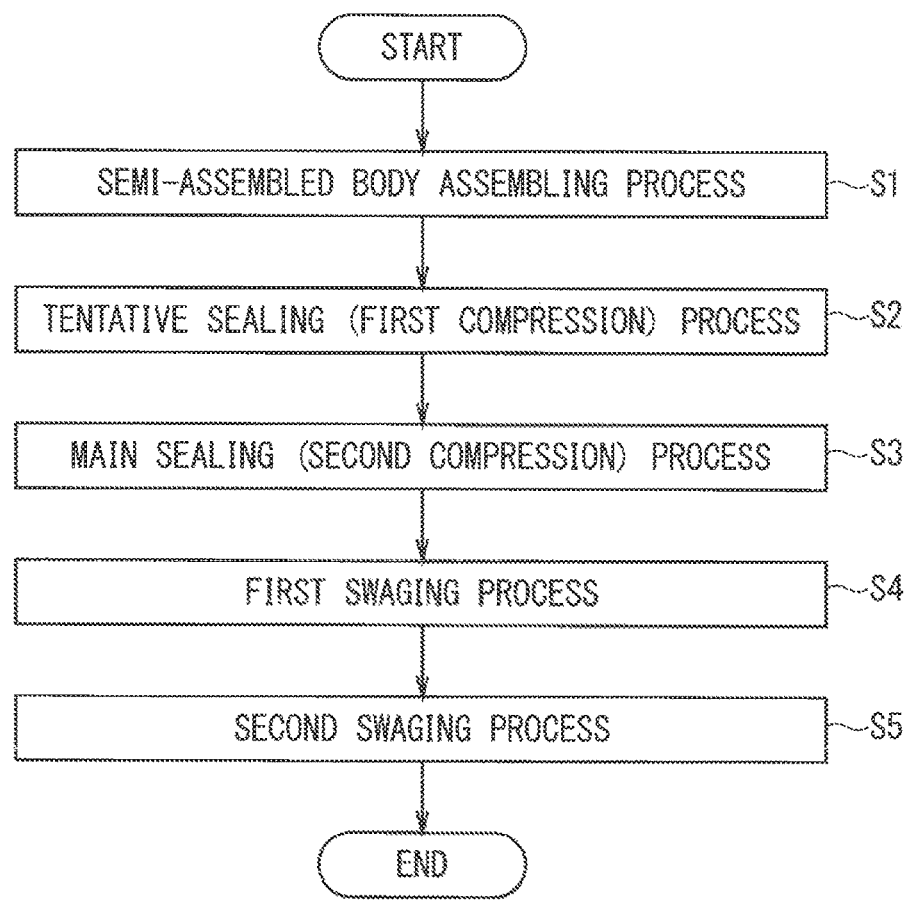
FIG. 3 is a view schematically illustrating a procedure of manufacturing an assembled body 40.

Next, there will be described a process of manufacturing the assembled body 40, which is a main subject in this preferred embodiment, in a process of manufacturing the gas sensor 1. FIG. 3 is a view schematically illustrating a procedure of manufacturing the assembled body 40.

The assembled body 40 is manufactured by performing the following processes, in the procedure shown in FIG. 3, on the semi-assembled body 40α assembled by a semi-assembled body assembling process (a step S1); performing the sealing process for hermetically sealing the inside of the semi-assembled body 40α in two stages, that is, the tentative sealing (the first compression) process (a step S2) and the main sealing (the second compression) process (a step S3), then forming the concave portion 6a in the inner tube 6 by the first swaging process (a step S41, and further forming the concave portion 6b in the inner tube 6 by the second swaging process (a step S5).

<Outline of Manufacturing Apparatus>

FIG. 4 is a block diagram schematically illustrating a structure of the manufacturing apparatus 100 for manufacturing the assembled body 40 by the procedure shown in FIG. 3.

The manufacturing apparatus 100 includes a control part 101 for controlling the overall operations of the manufacturing apparatus 100, which is constituted by a CPU 101a, a ROM 101b, a RAM 101c and the like, an operating part 102 being an input interface constituted by switches, buttons, a touch panel and the like for providing various types of execution commands to the manufacturing apparatus 100, a display part 103 constituted by a display and measuring instruments for displaying various types of operation menus and operation states of the manufacturing apparatus 100, and a storage part 104 storing an operation program 104p for the manufacturing apparatus 100 and operation condition data and the like which are not illustrated. In the manufacturing apparatus 100, the operation program 104p is executed by the control part 101, so that a series of operations which will be described later are performed through automatic processing.

As components for actually manufacturing the assembled body, the manufacturing apparatus 100 further includes a transportation part 110, a semi-assembled body assembling part 120, a tentative sealing processing part 130, a main sealing/swaging processing, part 140, and a retightening processing part 150.

The transportation part 110 is a part for transporting the semi-assembled body 40α and the assembled body 40 in the manufacturing apparatus 100. The transportation part 110 includes a transportation pallet 111 on which the semi-assembled body 40α and the assembled body 40 are disposed, a pallet movement mechanism 112 which moves the transportation pallet 111 to each part, by a predetermined procedure, and a pallet delivery mechanism 113 for delivering the transportation pallet 111, in which, the semi-assembled body 40α and the assembled body 40 are disposed, between each processing part.

The semi-assembled body assembling part 120 is a part for assembling the semi-assembled body 40α. The semi-assembled body assembling part 120 includes a first annularly-mounting mechanism 121 for annularly mounting the annularly-mounted members to the sensor element 10 to obtain the post-annularly-mounted assembly 31 and a second annularly-mounting mechanism 122 for annularly mounting the tubular body 30 to the post-annularly-mounted assembly 31 to obtain the semi-assembled body 40α.

Further, the semi-assembled body assembling part 120 includes an element standby part 123 and an annularly-mounted member standby part 124 in which the sensor element 10 and the annularly-mounted members (the washer 7, the ceramic supporter 8, and the powder compact 9), which are to be assembled, are disposed respectively, and also includes a tubular body standby part 125.

The tentative sealing processing part 130 is a part for performing the tentative sealing (the first compression), which is a processing for compressing the powder compact 9, mainly for purpose of positioning (fixing) the sensor element 10. The tentative sealing processing part 130 includes a pallet mounting stand 131 on which the transportation pallet 111 is disposed, an element positioning pin 132 for positioning the sensor element 10 at the time of the tentative sealing, a first adjustment jig 133A and second adjustment jig 133B for adjusting a position of the sensor element 10 in a horizontal plane prior to the tentative sealing, and a tentative sealing jig (a first compression jig) 134 for, pressing the washer 7 at the time of the tentative sealing.

The tentative sealing processing part 130 further includes a positioning pin elevating mechanism 132m for performing operations for elevating the element positioning pin 132 in a vertical direction, an in-plane position adjustment mechanism 133m for performing operations for adjusting an in-horizontal-plane position of the sensor element 10 using the first adjustment jig 133A and the second adjustment jig 133B, and a tentative sealing jig elevating mechanism 134m for performing operations for elevating the tentative sealing jig 134 in the vertical direction.

The main sealing/swaging processing pan 140 is a part for performing the main sealing (the second compression) to secure the airtightness (hermetic sealing) between the measurement gas space and the reference gas space in the gas sensor 1 and forming the concave portion 6a by swaging the inner tube 6 (the first swaging). The main sealing/swaging processing part 140 includes a pallet mounting stand 141 on which the transportation pallet 111 is disposed, a main sealing jig 142 for pressing the washer 7 at the time of the main sealing, and a first swaging jig 143 for swaging the inner tube 6 to form the concave portion 6a.

The main sealing/swaging processing part 140 further includes a mounting stand elevating mechanism 141m for performing operations for elevating the pallet mounting stand 141 in the vertical direction and a swaging jig movement mechanism 143m for performing operations for moving the first swaging jig 143 in a horizontal plane.

The retightening processing part 150 is a part for forming the concave portion 6b by swaging the inner tube 6 (the second swaging). In this preferred embodiment, referred to as a retightening is the formation, in the inner tube 6, of the concave portion 6b in the second swaging process subsequent to the formation of the concave portion 6a in the first swaging process. The retightening processing part 150 includes pallet mounting stand 151 on which the transportation pallet 111 is disposed, a retightening assist jig 152 abutting on the washer 7 at the time of the retightening, and a second swaging jig 153 for swaging the inner tube 6 to form the concave portion 6b.

The retightening processing part 150 further includes a mounting stand elevating mechanism 151m for performing operations for elevating the pallet mounting stand 151 in the vertical direction and a swaging jig movement mechanism 153m for performing operations for moving the second swaging jig 153 in a horizontal plane.

<Assembly of Intermediate Member>

A detailed description of the manufacturing the assembled body 40 performed by the procedure shown in FIG. 3 is sequentially provided hereinafter.

Figure 5A:
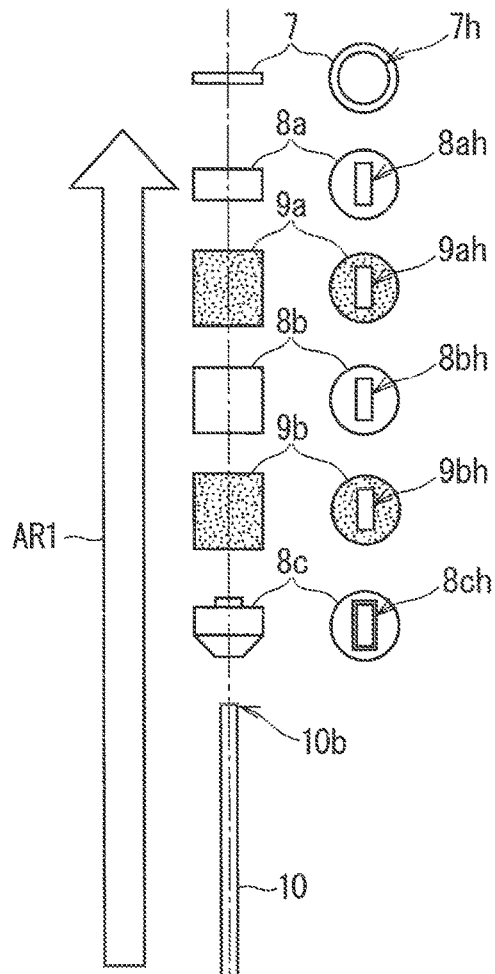
FIGS. 5A to 5C are views schematically illustrating a semi-assembled body assembling process.
Figure 5B:
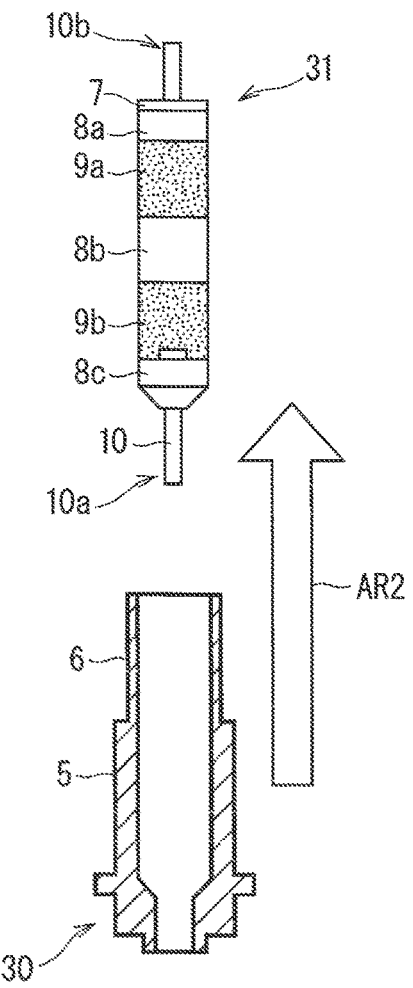
Figure 5C:
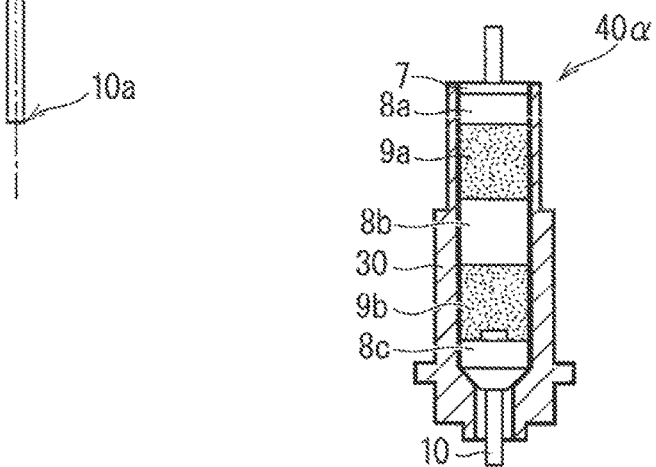

FIGS. 5A to 5C are views schematically illustrating a semi-assembled body assembling process performed in the semi-assembled body assembling part 120 (the step S1 in FIG. 3).

In the semi-assembled body assembling process, firstly, the first annularly-mounting mechanism 121 obtains the sensor element 10 from the element standby part 123 and holds the sensor element 10 using a holding means not shown in the drawings. Subsequently, the first annularly-mounting mechanism 121 obtains the washer 7, the ceramic supporter 8a, the powder compact 9a, the ceramic supporter 8b, the powder compact 9b, and the ceramic supporter 8c from the annularly-mounted member standby part 124 in this order and then annularly mounts them to the sensor element 10 from the first tip portion 10a side of the sensor element 10 as indicated by an arrow AR1 in FIG. 5A. Accordingly, the post-annularly-mounted assembly 31 shown in FIG. 5B is obtained. The sensor element 10 and each annularly-mounted member are manufactured in a predetermined place in advance and prepared in the element standby pan 123 and the annularly-mounted member standby part 124, respectively, prior to the execution of the semi-assembled body assembling process.

More specifically, each annularly-mounted member has a disc shape or cylindrical shape. For annularly mounting as described above, a circular through hole 7h is provided at the axis center position of the washer 7, and through holes 8ah, 9ah, 8bh, 9bh, and 8ch having a rectangular shape corresponding to the cross-sectional shape of the sensor element 10 are provided in the ceramic supporter 8a, powder compact 9a, ceramic supporter 8b, powder compact 9b, and ceramic supporter 8c, respectively. Those through holes are fitted with the sensor element 10, so that the members are each annularly mounted to the sensor element 10. In the above case, the washer 7, ceramic supporters 8, and powder compacts 9 are coaxially arranged.

From the point of securing the airtightness, the through holes of the ceramic supporters 8 and the through holes of the powder compacts 9 are configured such that a difference with a design cross-sectional size of the sensor element 10 is 0.25 to 0.35 mm and a dimensional tolerance is 0.1 mm. Meanwhile, the through hole 7h of the washer 7 is provided so as to have a difference with the design cross-sectional size of the sensor element 10 of at least 1 mm or more and 13 mm or less. The washer 7, ceramic supporters 8, and powder compacts 9 are configured to have a difference in outside diameter value of approximately 0.35 mm at a maximum.

Next, the second annularly-mounting mechanism 122 obtains the tubular body 30 from the tubular body standby part 125 to annularly mount it to the post-annularly-mounted assembly 31 from an inner tube 6 side. Specifically, the tubular body 30 is annularly mounted to the post-annularly-mounted assembly 31 from a side providing the first tip portion 10a of the sensor element 10, as indicated by an arrow AR2 in FIG. 5B. Accordingly, the semi-assembled body 40α shown in FIG. 5C is obtained. At this time, since the semi-assembled body 40α is not sealed yet, the sensor element 10 is not completely fixed. Accordingly, the sensor element 10 can be displaced in the longitudinal direction due to an action of an external force, for example. In other words, in the semi-assembled body 40α which is not yet sealed, the sensor element 10 is not positioned. The sensor element 10 is positioned in the tentative sealing process performed in a next step.

<Transportation and Delivery by Transportation Part>

The semi-assembled body 40α assembled in the semi-assembled body assembling part 120 is then transported by the transportation part 110 and is delivered between the transportation part 110 and respective parts performing processing in subsequent stages.

FIG. 6 is a planar view schematically illustrating a transportation of the semi-assembled body 40α and the assembled body 40 in the transportation part 110 and the delivery of the semi-assembled body 40α and the assembled body 40 between the transportation part 110 and respective parts.

In outline, the transportation part 110 is configured such that the semi-assembled body 40α and the assembled body 40 are transported in a state of being disposed on the transportation pallet 111, and the delivery of the semi-assembled body 40α or the assembled body 40 between the transportation part 110 and respective parts is performed together with the transportation pallet 111 on which the semi-assembled body 40α or the assembled body 40 is disposed.

A fitting part 111a is provided in an upper part of the transportation pallet 111, and the semi-assembled body 40α or the assembled body 40 is fitted with the fitting part 111a, so that the semi-assembled body 40α or the assembled body 40 is disposed on and fixed to the transportation pallet 111. More specifically, a lower portion of the tubular body 30 of the semi-assembled body 40α or the assembled body 40 in such a posture that its side provided with the washer 7 is directed upward is fitted into the fitting part 11 so that the semi-assembled body 40α or the assembled body 40 is disposed on and fixed to the transportation pallet 111 (refer to FIGS. 8A and 8B, for example.) In this preferred embodiment, the lower portion of the tubular body 30 indicates the projection 5b and a part located below the projection 5b in the housing 5 in FIG. 2. In other words, the semi-assembled body 40α and the assembled body 40b are transported by the transportation pallet 111 in such a posture that the longitudinal direction of the sensor element 10 extends in the vertical direction and its side provided with the second tip portion 10b is directed upward. Such a posture of the semi-assembled body 40α and the assembled body 40 is also referred to as an assembly posture.

The semi-assembled body 40α and the assembled body 40 are preferably positioned so that a rotational deviation is prevented in the horizontal plane at the time of the disposition and fixing. This may be achieved by causing an outer periphery shape of the housing 5 to have anisotropy and also causing the fitting part 111a to have a shape corresponding to the outer periphery shape, or the holding means (not shown) included in, the transportation pallet 111 may hold a horizontal posture of the semi-assembled body 40α and the assembled body 40.

In the transportation part 110, determined in advance are a first delivery position Pos1 for receiving the assembled semi-assembled body 40α from the semi-assembled body assembling pan 120 and second delivery position Pos2 to fourth delivery position Pos4 for delivering the semi-assembled body 40α or the assembled body 40 between the transportation part 110 and the tentative sealing processing part 130, the main sealing/swaging processing part 140, and the retightening processing part 150, respectively.

The tentative sealing processing part 130, the main sealing/swaging processing part 140, and the retightening processing part 150 are provided with the pallet mounting stands 131, 141, and 151 which the transportation pallet 111 is disposed on and fixed to, respectively. The pallet mounting stands 131, 141, and 151 include pallet fitting parts 131a, 141a, and 151a, respectively, and the transportation pallet 111 is fitted into these pallet fining parts 131a, 141a, and 151a in each processing part to achieve a state where the transportation pallet 111 is disposed on and fixed to the pallet mounting stands 131, 141, and 151.

The pallet movement mechanism 112 (not shown in FIG. 6) firstly places the transportation pallet 111 in the first delivery position Pos1 at a timing of assembling the semi-assembled body 40α in the semi-assembled body assembling pan 120. The obtained semi-assembled body 40α is delivered to the transportation pallet 111 disposed in the first delivery position Pos1, as indicated by an arrow AR3, by the pallet delivery mechanism 113 not shown in FIG. 6.

Subsequently, alternately performed are the transport of the transportation pallet 111 to the second delivery position Pos2 to fourth delivery position Pos4 performed by the pallet movement mechanism 112 indicated by arrows AR4 to AR6 and the delivery of the transportation pallet 111 between each delivery position and pallet mounting stand performed by the pallet delivery mechanism 113 indicated by arrows AR7 to AR9 in FIG. 6.

When the transportation pallet 111 is returned from the retightening processing part 150 to the fourth delivery position Pos4 after the completion of the processing in the retightening processing part 150, the assembled body 40 held by the transportation pallet 111 is delivered to an assembled body standby part 170. Alternatively, the assembled body 40 may be subsequently transported to the other processing part. The transportation pallet 111 which has become empty is returned to the first delivery position Pos1 and is then used in the subsequent processing again.

Alternatively, it is also applicable that the transportation pallet 111 which has transported the semi-assembled body 40α or the assembled body 40 from a previous delivery position to a delivery position corresponding to a certain processing part is different from the transportation pallet 111 which transports the semi-assembled body 40α or the assembled body 40 to a next delivery position after the completion of the processing in the processing part.

<Tentative Sealing>

The semi-assembled body 40α which has been assembled in the semi-assembled body assembling part 120 is provided to the tentative sealing (the first compression) process (the step S2 in FIG. 3) performed in the tentative sealing processing part 130. The tentative sealing process is a process performed mainly for purpose of tentatively fixing the sensor element 10 in a position where the sensor element 10 abuts to the element positioning pin 132. The term "tentative" is used herein by reason that a slight displacement of the sensor element 10 occurs at the time of the main sealing (the second compression) which is to be performed subsequently.

FIG. 7 is a view illustrating a more specific procedure of the tentative sealing process. FIGS. 8 to 11 are views illustrating states halfway through the tentative sealing process in stages.

Figure 8A:
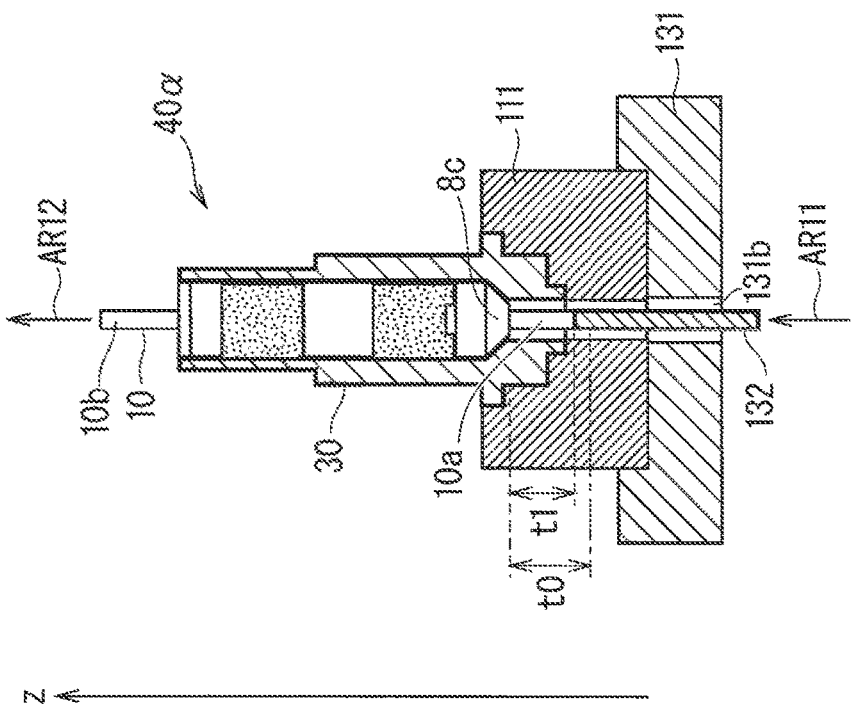
FIGS. 8A and 8B are views illustrating a state halfway through the tentative sealing process in stages.

FIG. 8A illustrates a state where the transportation pallet 111 holding (placing and fixing) the semi-assembled body 40α is disposed on the pallet mounting stand 131.

In performing the tentative sealing process in the tentative processing part 130, firstly, the transportation pallet 111, which has been delivered from the semi-assembled body assembling part 120 in the first delivery position Pos1 and holds (places and fixes) the semi-assembled body 40α, is disposed on the second delivery position Pos2 by the pallet movement mechanism 112, and then, the transportation pallet 111 is disposed on and fixed to the pallet mounting stand 131 in the tentative sealing processing part 130 together with the semi-assembled body 40α, by the pallet delivery mechanism 113, as shown in FIG. 8A (a step S21).

Figure 8B:
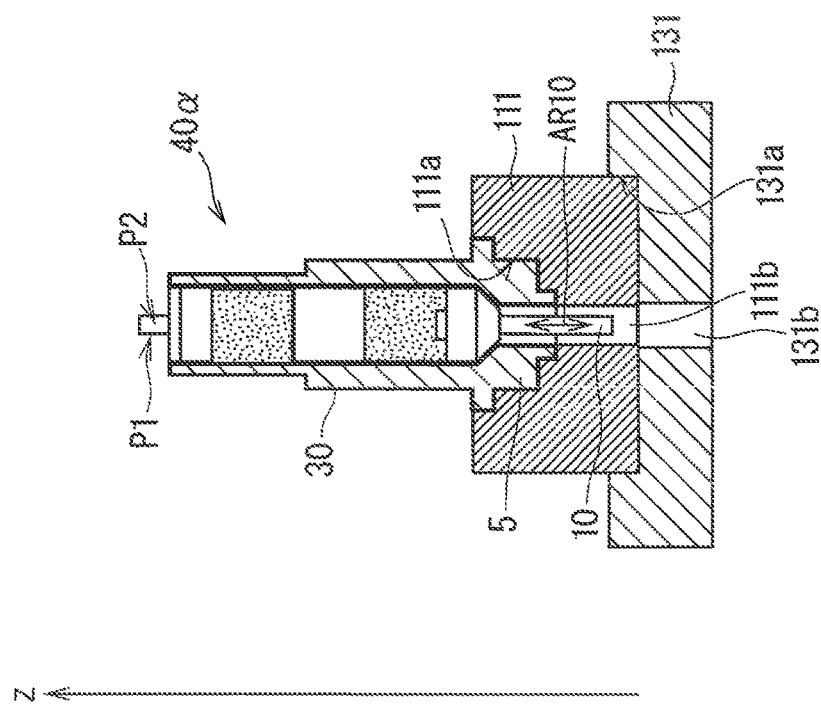

FIGS. 8A and 8B illustrate a state where the semi-assembled body 40α is disposed and fixed in the assembly posture, in which a thickness direction of the sensor element 10 coincides a horizontal direction of FIGS. 8A and 8B, in other words, the main surface P1 is perpendicular to the horizontal direction of FIGS. 8A and 8B, and one of the side surfaces P2 is directed to a near side of FIGS. 8A and 8B. The state where the transportation pallet to which the semi-assembled body 40α is placed and fixed is disposed on and fixed to the pallet mounting stand 131 is also referred to simply as a state where the semi-assembled body 40α is fixed to the pallet mounting stand 131. In FIGS. 8A and 8B and subsequent drawings, a coordinate in which a vertical upper side is defined as a forward direction of a z axis is illustrated, appropriately.

As, shown in FIGS. 8A and 8B, a hole part 111b is provided in a lower, side of the fitting part 111a in the transportation, pallet 111 to prevent the sensor element 10 protruding in a lower side of the semi-assembled body 40α from interfering with the transportation pallet 111. In addition, the pallet mounting stand 131 also includes a hole part 131b in a lower side of the pallet fitting part 131a. The hole part 131b is provided so as to come to be coaxial with the hole part 111b of the transportation pallet 111 at the time when the transportation pallet 111 is disposed on the pallet fitting part 131a.

As described above, since the sensor element 10 is not positioned, it can be displaced up and down in the hole part 111b and further in the hole part 131b as indicated by an arrow AR10. Although not shown in the drawings, the hole part 131b has a configuration that the sensor element 10 does not protrude from the transportation pallet 111.

The hole parts 111b and 131b are also used as a space of elevating the element positioning pin 132. Although not shown in FIG. 8A, the element positioning pin 132 has a configuration that it can be elevated in the vertical direction in the positioning pin elevating mechanism 132m and can enter the hole parts 111b and 131b.

When the semi-assembled body 40α is fixed to the pallet mounting stand 131, the positioning pin, elevating mechanism 132m raises the element positioning pin 132 to the vertical upper side in the hole part 131b and the hole part 111b as indicated by an arrow AR11 in FIG. 8B to place the element positioning pin 132 in a predetermined position (a step S22).

More specifically, when a target value of a distance between a lowermost end of the ceramic supporter 8c and a lowermost end of the sensor element 10 (the end in the first tip portion 10a side) under a state that the assembled body 40 is hermetically sealed finally (referred to as a protruding length) is defined as t0, the element positioning pin 132 is disposed so that the protruding length is set to t1 which is shorter than t0. Accordingly, the sensor, element 10 is pushed up as indicated by an arrow AR12, so that the second tip portion 10b protrudes from the tubular body 30. The position where the sensor element 10 is located at this time is defined as a first position.

Such a placement of the sensor element 10 in the first position where the protruding length is t1 due to pushing up the lowermost end of the sensor element 10 with the element positioning pin 132 is performed in consideration of the shifting that the sensor element 10 descends from the first position in the process in the subsequent stages, and the protruding length gets closer to t0. A difference between the protruding lengths t0 and t1 is experimentally determined in advance.

When the element positioning pin 132 is disposed in a side of the first tip portion 10a of the sensor element 10, as shown in FIGS. 9A and 9B, the position of the sensor element 10 in the horizontal plane is adjusted in a side of the second tip portion 10b of the sensor element 10 by the first adjustment jig 133A and the second adjustment jig 133B (a step S23). The above adjustment is performed in two stages, that is, an adjustment in the thickness direction of the sensor element 10 performed by the first adjustment jig 133A and an adjustment in a width direction of the sensor element 10 performed by the second adjustment jig 133B.

Firstly, with the operation of the in-plane position adjustment mechanism 133m not shown in FIGS. 9A and 9B, a pair of first adjustment jigs 133A performs the position adjustment of the sensor element 10 in the thickness direction as shown in FIG. 9A. Specifically, as can be seen from a top view shown in a frame indicated by an arrow AR13, each of the pair of the first adjustment jigs 133A is provided so as to be movable in an x axial direction as indicated by an arrow AR14. The pair of the first adjustment jigs 133A abuts to the main surface P1 of the sensor element 10 and sandwich the sensor element 10 therebetween, so that the sensor element 10 is positioned (centered) in the thickness direction.

Subsequently, in the similar manner, with the operation of the in-plane position adjustment mechanism 133m not shown in FIGS. 9A and 9B, a pair of second adjustment jigs 133B performs the position adjustment of the sensor element 10 in the width direction as shown in FIG. 9B. Specifically, as can be seen from a top view shown in a frame indicated by an arrow AR15, each of the pair of the second adjustment jigs 133B is provided so as to be movable in a y axial direction as indicated by an arrow AR16. The pair of the second adjustment jigs 133B abut to the side surface P2 of the sensor element 10 and sandwich the sensor element 10 therebetween, so that the sensor element 10 is positioned (centered) in the width direction.

After the position of the sensor element 10 in the horizontal plane is determined, the tentative sealing (the first compression) is subsequently performed by the tentative sealing jig 134 as shown in FIGS. 10A and 10B (a step S24).

The tentative sealing jig 134 is provided so as to he elevated in the vertical direction by the tentative sealing jig elevating mechanism 134m not shown in FIGS. 10A and 10B, in a position which is located in, a vertical upper side of the semi-assembled body 40α (more specifically, the sensor element 10) under the state that the semi-assembled body 40α is fixed to the pallet mounting stand 131. The tentative sealing jig 134 includes a substantially annular abutting part 134a, which comes to abut to the washer 7 which constitutes the semi-assembled body 40α from its upper side, in a lowermost end thereof in the vertical direction, and, a cavity part 134b which opens toward a vertically lower side. The tentative sealing jig 134 is disposed coaxially with the semi-assembled body 40α fixed to the pallet mounting stand 131.

The cavity part 134b is a part in which the sensor element 10 is housed at the time of the tentative sealing. The cavity part 134b is provided to prevent interference between the tentative sealing jig 134 and the sensor element 10 when the tentative sealing jig 134 descends for the tentative sealing.

The tentative sealing is achieved by lowering the tentative sealing jig 134 from the upper side of the semi-assembled body 40α toward the vertically lower side as indicated by an arrow AR17 in FIG. 10A, with the tentative sealing jig elevating mechanism 134m not shown in FIGS. 10A and 10B.

When the tentative sealing elevating mechanism 134m lowers the tentative sealing jig 134, the abutting part 134a of the tentative sealing jig 134 abuts to the washer 7 in due course. At this time, the sensor element 10 is housed in the cavity part 134b.

The tentative sealing jig elevating mechanism 134m continues to lower the tentative sealing jig 134 as indicated by an AR18 in FIG. 10B after the abutting part 134a abuts to the washer 7. The abutting part 134a of the tentative sealing jig 134 thereby presses the washer 7 to apply a vertically downward force (load) F1 (a first force) to the washer 7. Herein, the force F1 is applied within a range that the sensor element 10 can be fixed but a chip (or a break) does not occur in the sensor element 10. The actual value of the force F1 may be set in view of an area of the abutting part 134a which abuts to the washer 7.

When the force F1 acts on the washer 7 from the abutting part 134a, the washer 7 is slightly pushed vertically downward, and the force F1 also acting on the powder compacts 9a and 9b via the ceramic supporters 8a and 8b acts as a compression force. The powder compacts 9a and 9b are thereby compressed. In accordance with the compression, a gap between the powder compacts 9a and 9b and the sensor element 10 disappears, and the powder compacts 9a and 9b are attached firmly to the sensor element 10. Then, the sensor element 10 which has been displaceable in the vertical direction is fixed by the powder compacts 9a and 9b. Since the sensor element 10, which is positioned by the element positioning pin 132, is kept in the first position, the sensor element 10 is fixed, as a result, to the first position at which the protruding length in the lowermost end of the sensor element 10 is t1.

Figure 11:
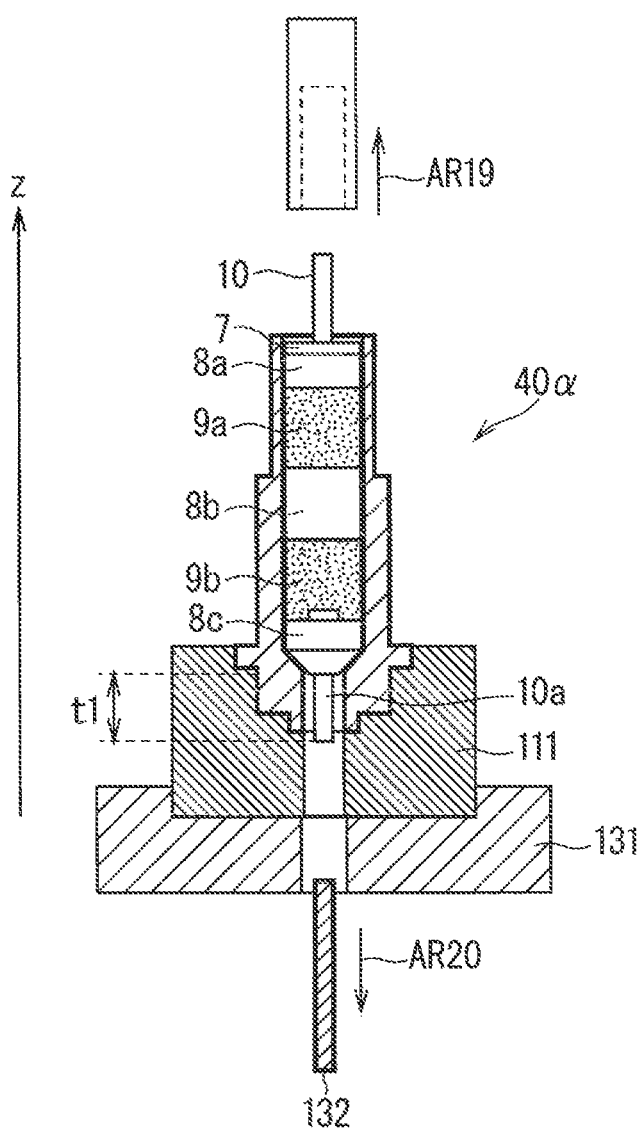
FIG. 11 is a view illustrating a state halfway through the tentative sealing process in stages.

After the tentative sealing is finished, as indicated by arrows AR19 and AR20 in FIG. 11, the tentative sealing jig 134 and the element positioning pin 132 are sequentially taken off (a step S25). Then, the transportation pallet 111 holding the semi-assembled body 40α, on which the tentative sealing has been performed, is delivered from the pallet mounting stand 131 to the pallet movement mechanism 112 by the pallet deliver mechanism 113 (a step S26). That is to say, the transportation pallet 111 is disposed in the second deliver position Pos2 again. The tentative sealing process is thereby finished.

<Main Sealing and First Swaging>

The semi-assembled body 40α on which the tentative sealing is performed, in the tentative sealing processing part 130 is provided to the main sealing (the second compression) process (the step S3 in FIG. 3) and the subsequent first swaging process (the step S4 in FIG. 3) performed in the main sealing/swaging processing part 140. The main sealing process is a process performed mainly for purpose of securing the airtightness between the measurement gas space and the reference gas space. The first swaging process is a process performed for completely constraining the annularly-mounted member in the tubular body 30 of the main-sealed semi-assembled body 40α.

Figure 12:
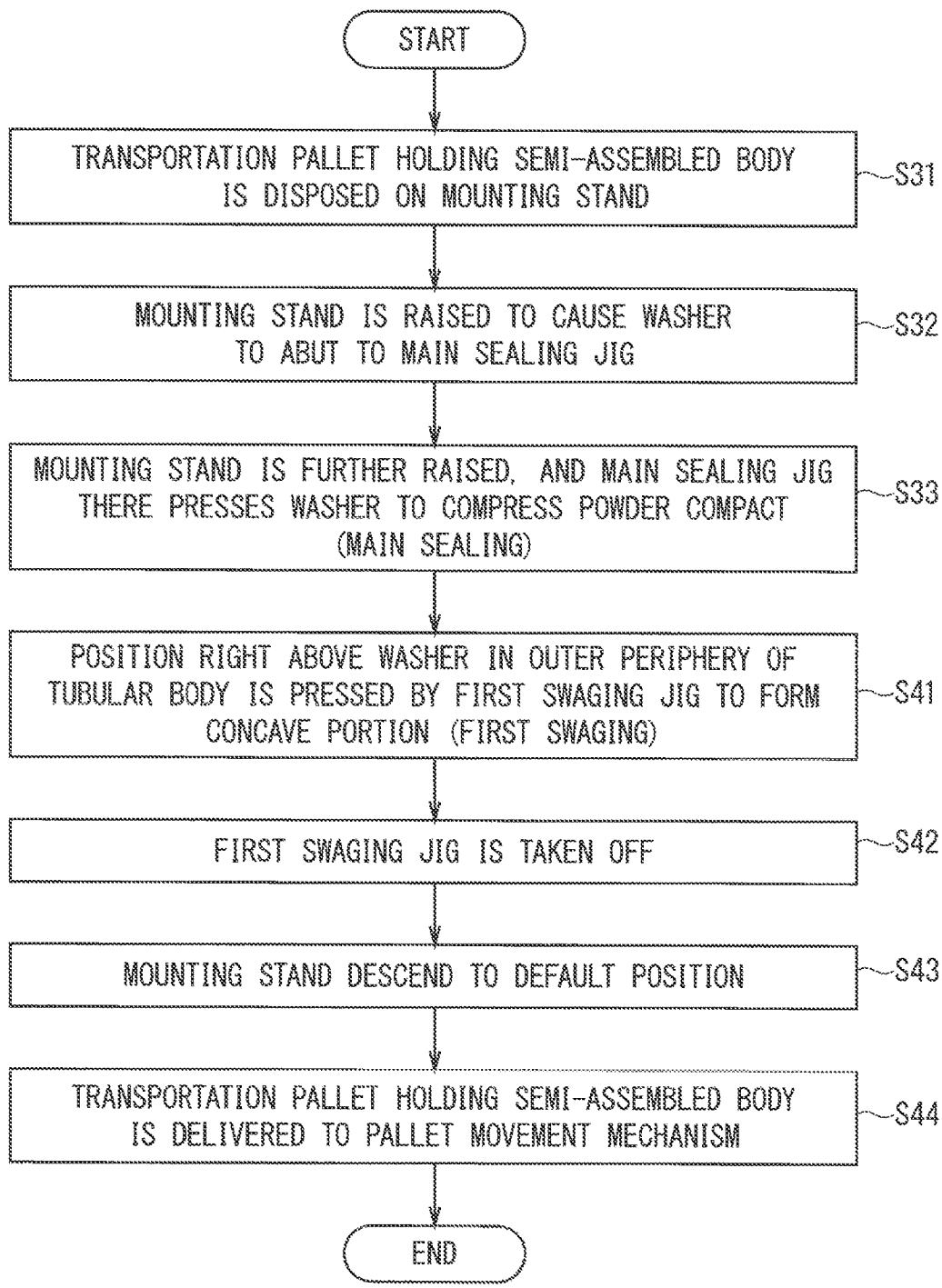
FIG. 12 is a view illustrating a more specific procedure of a main sealing process and a first swaging process.
Figure 13:
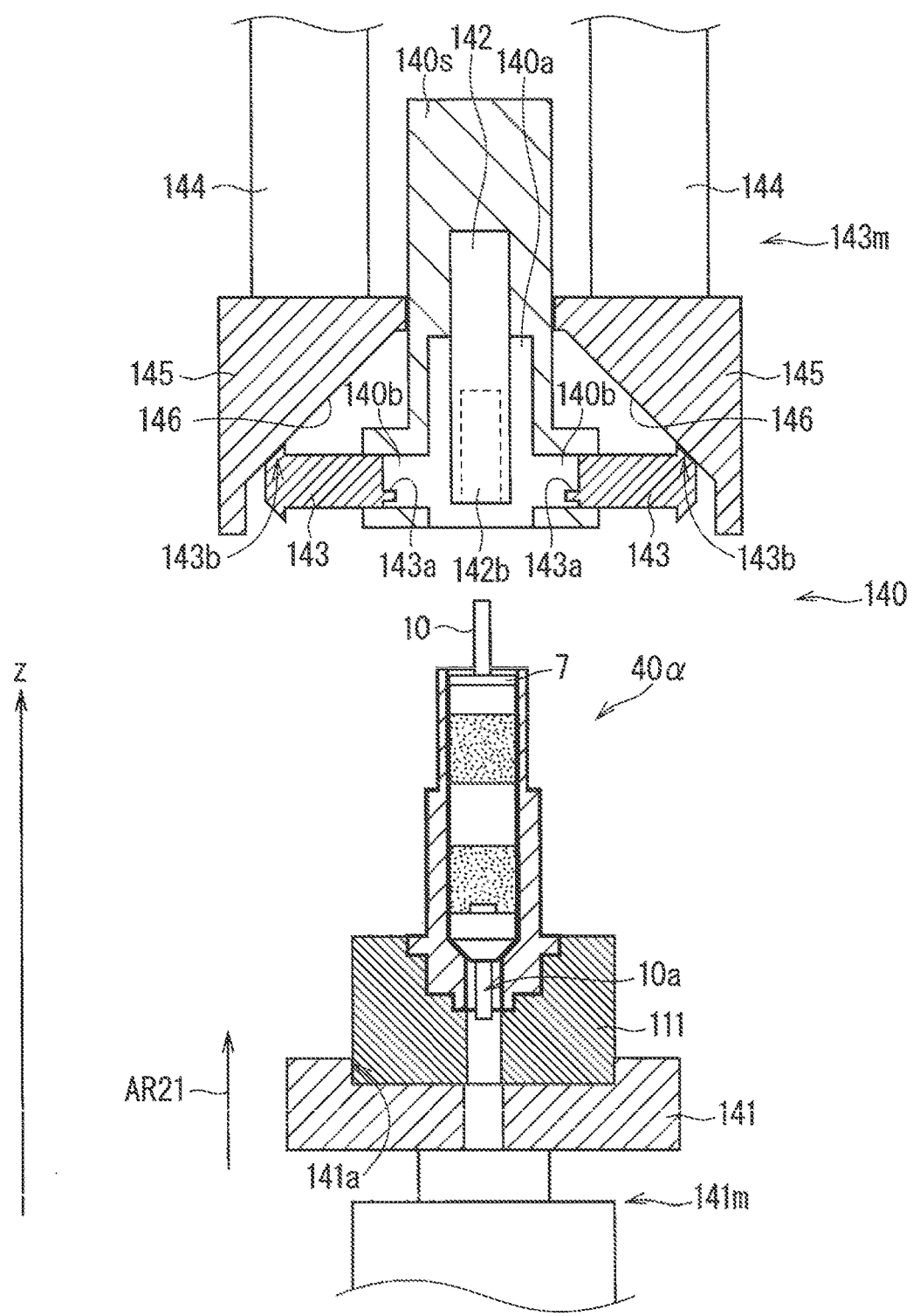
FIG. 13 is a side view schematically illustrating a structure of a main sealing/swaging processing part 140.
Figure 14:
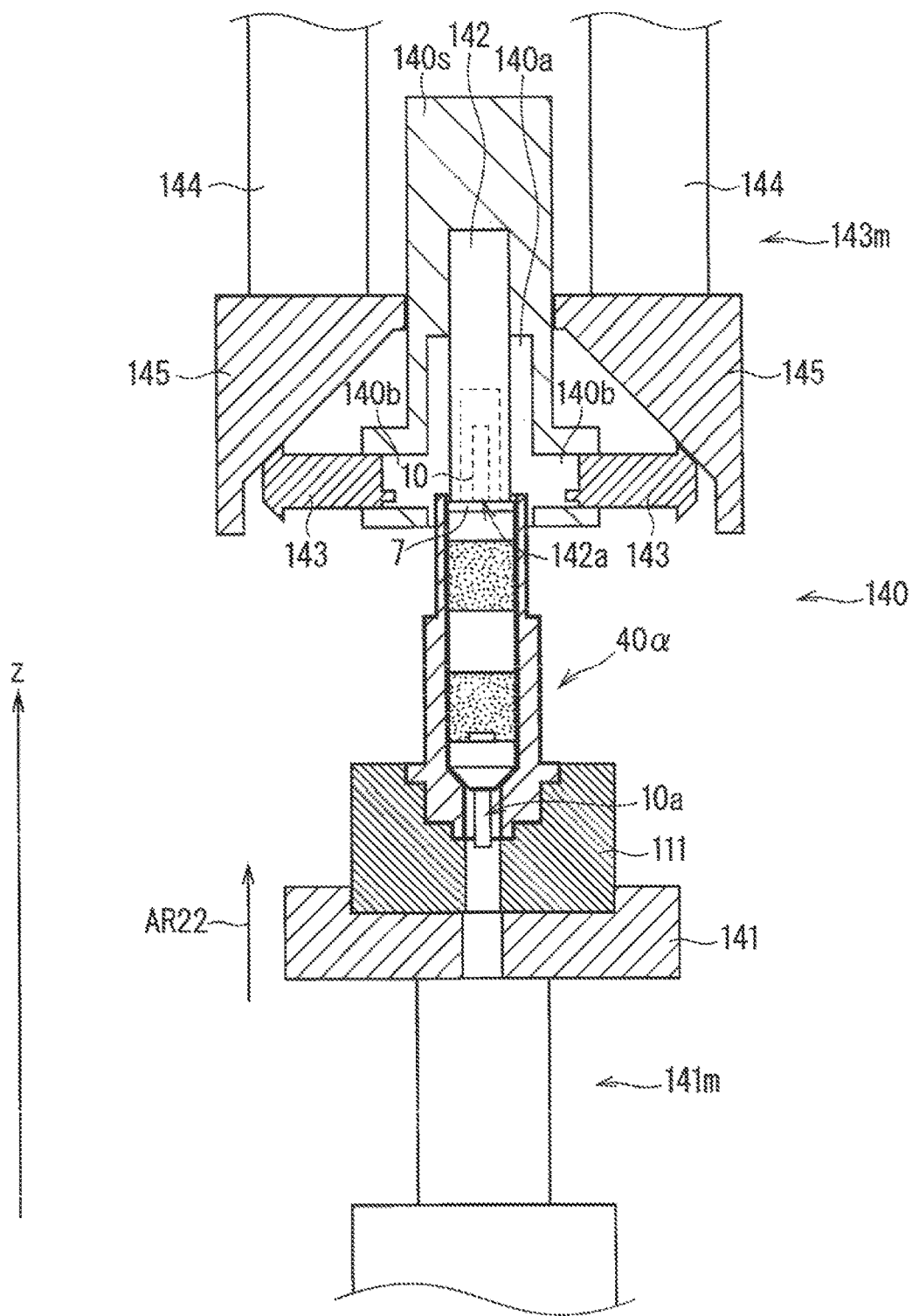
FIG. 14 is a view illustrating a state halfway through the main sealing process in stages.
Figure 15:
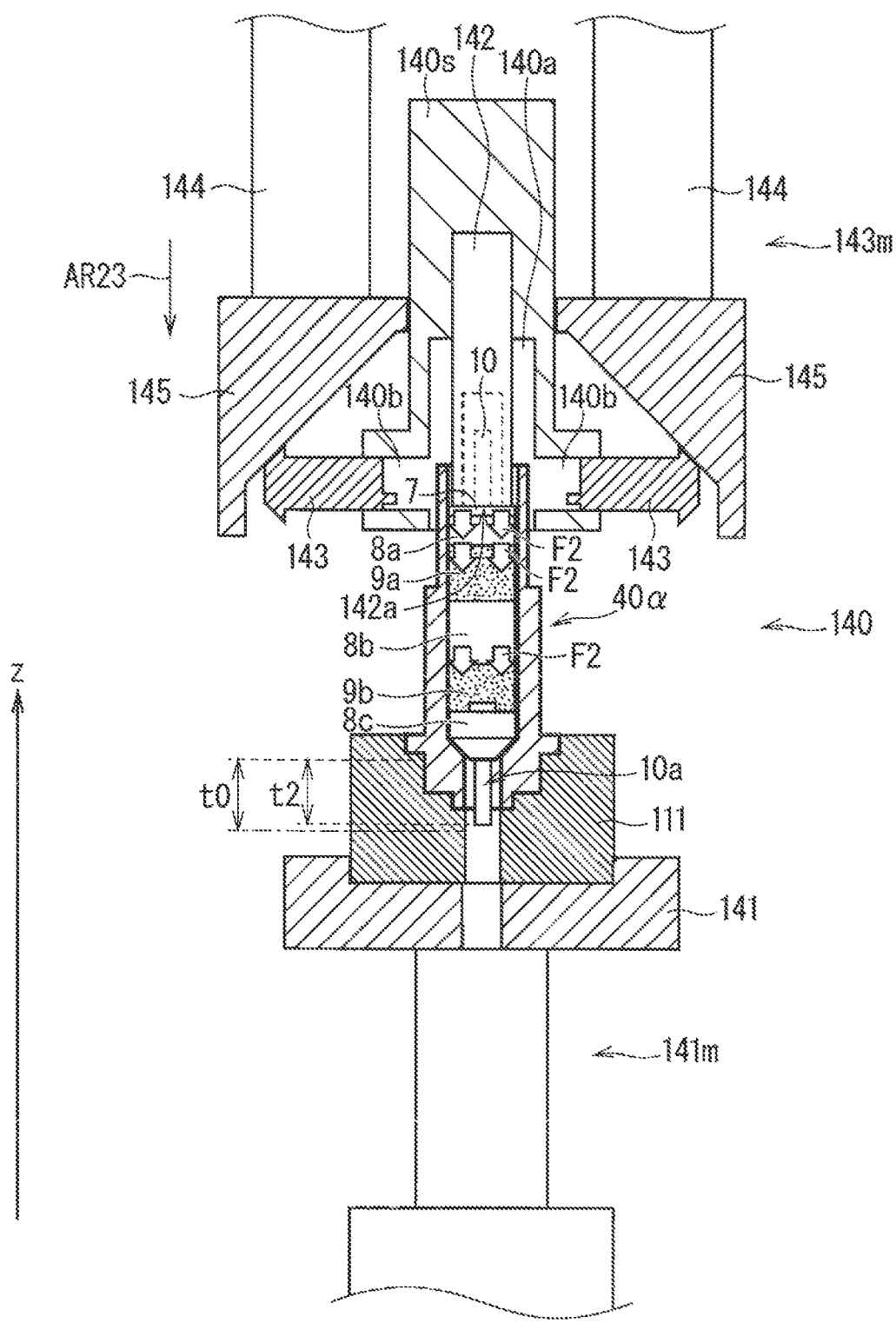
FIG. 15 is a view illustrating a state halfway through the main sealing process in stages.
Figure 16:
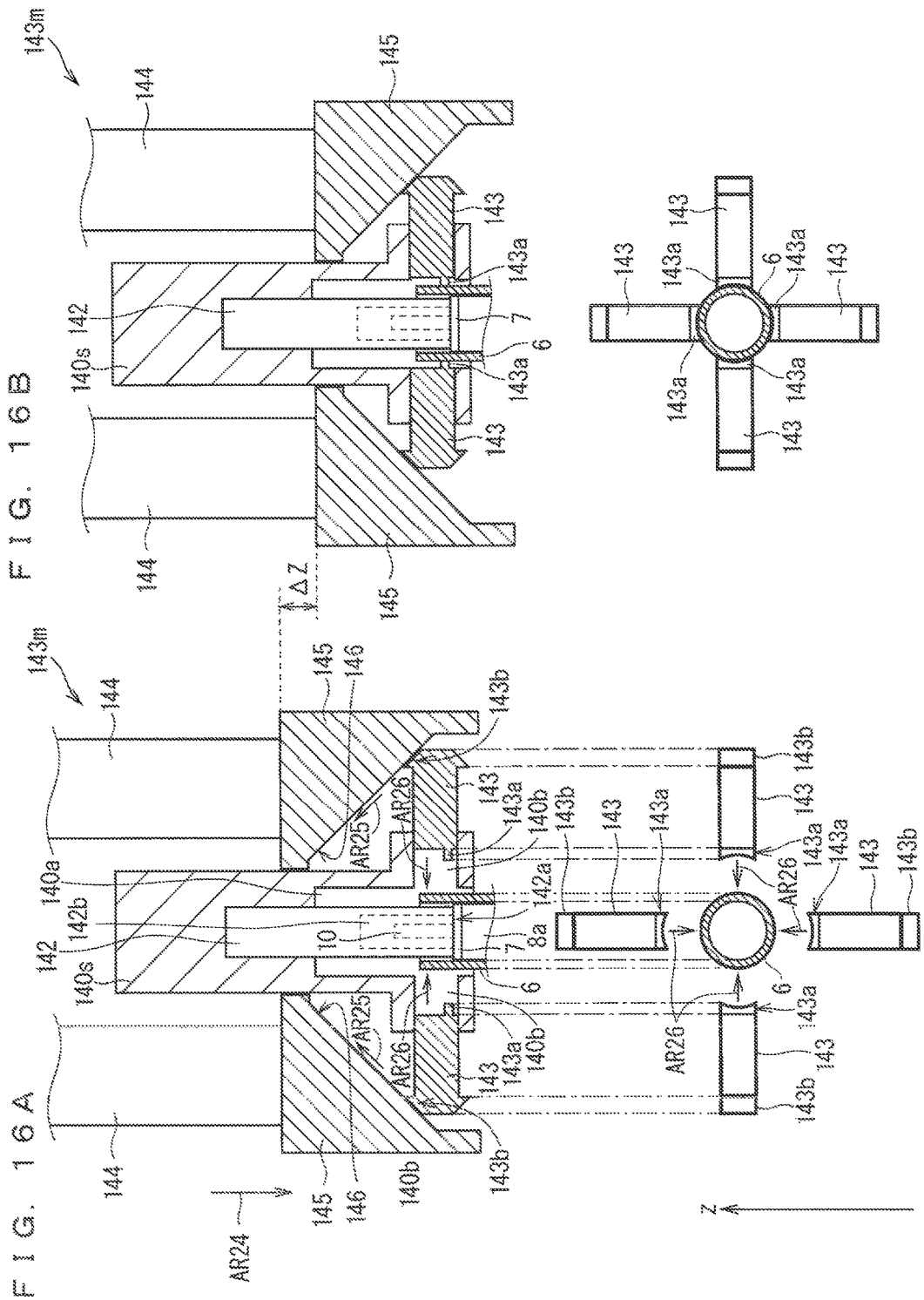
FIGS. 16A and 16B are views for describing an operation of a swaging jig movement mechanism 143m at the time of the first swaging.
Figure 17:
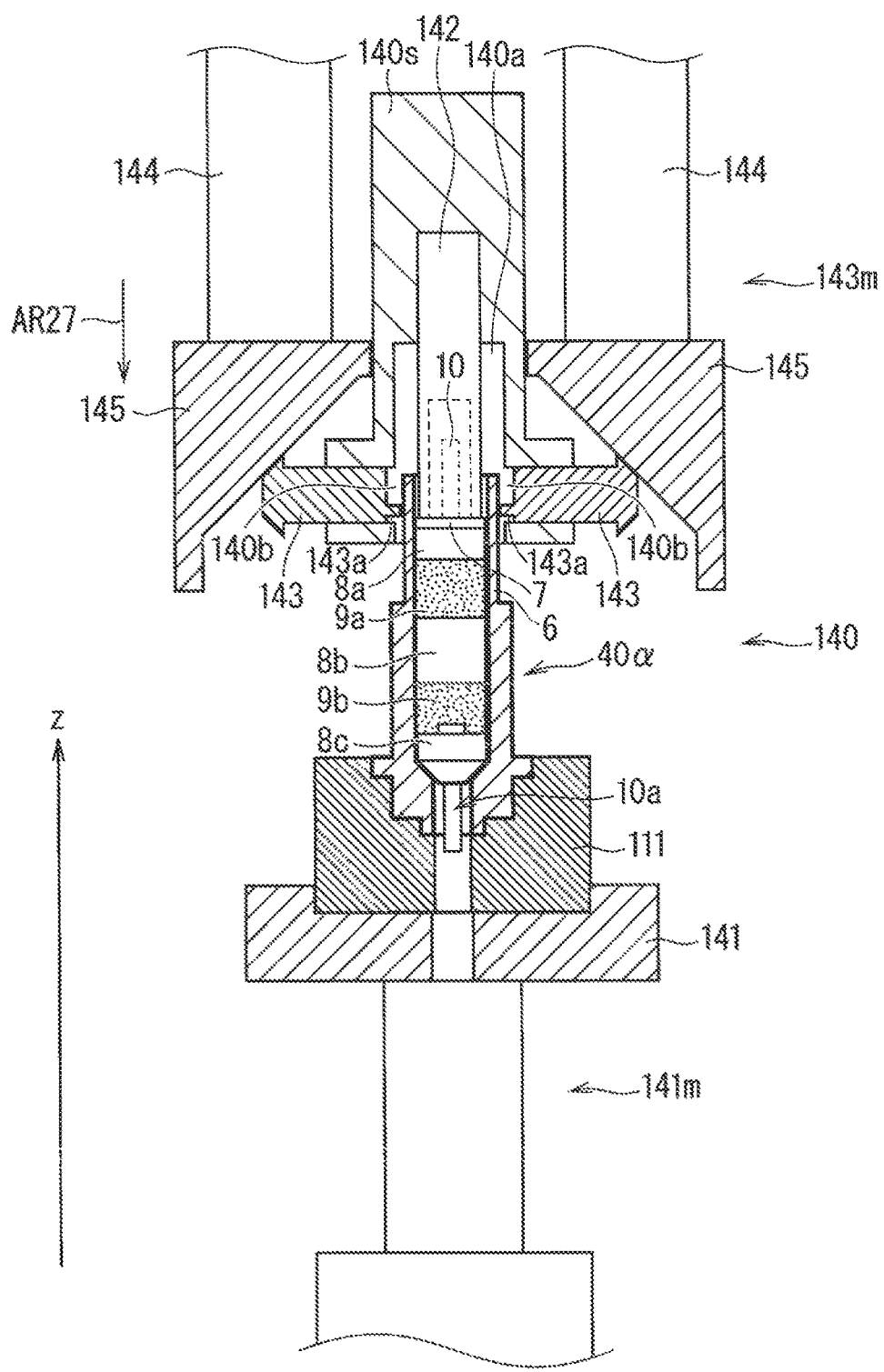
FIG. 17 is a view illustrating a state halfway through the first swaging process in stages.
Figure 18:
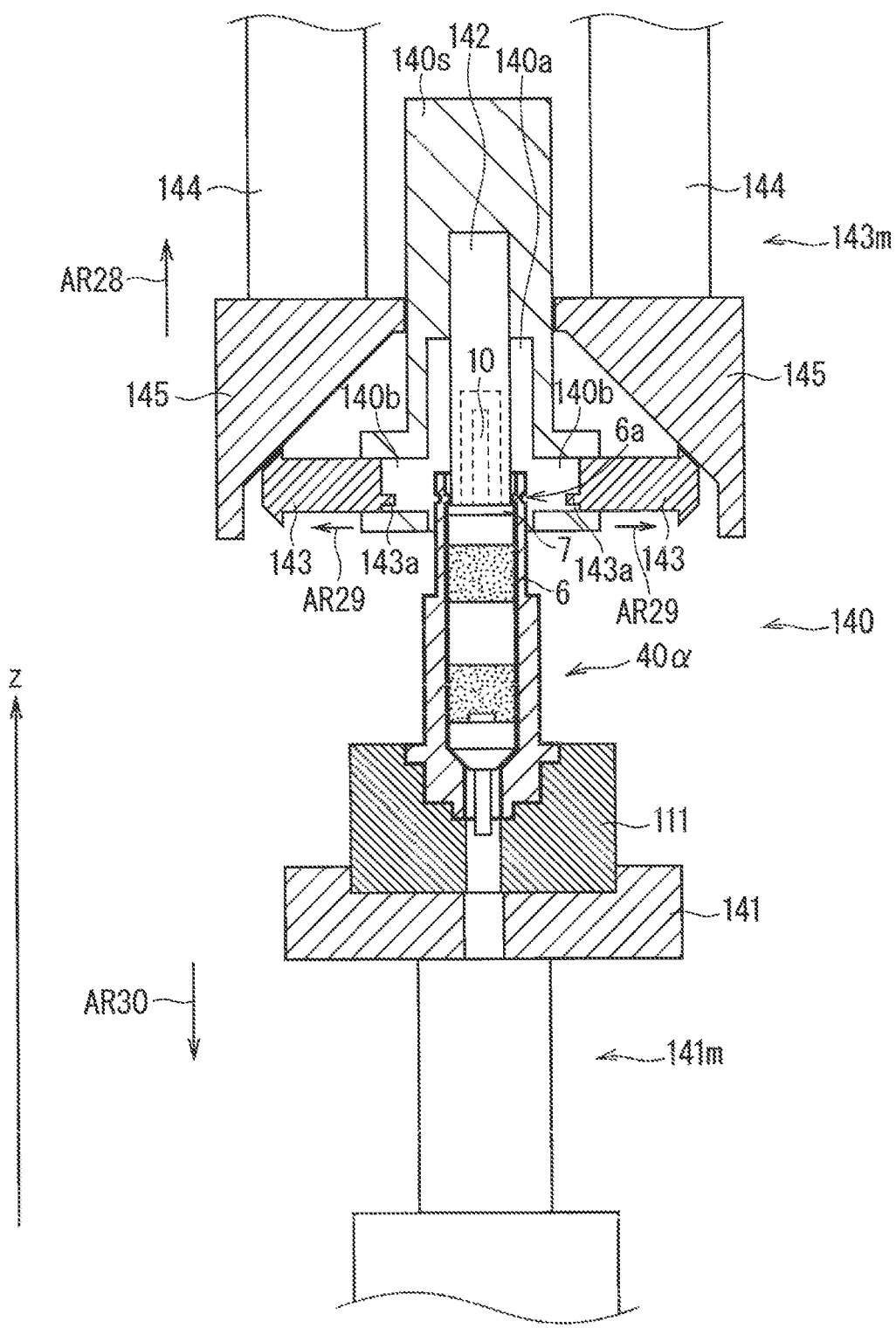
FIG. 18 is a view illustrating a state halfway through the first swaging process in stages.

FIG. 12 is a view illustrating a more specific procedure of the main sealing (the second compression) process and the first swaging process. The main sealing process and the first swaging process are sequentially performed in the main sealing/swaging processing part 140. FIG. 13 is a side view (a partial cross sectional view) schematically illustrating a structure of the main sealing/swaging processing part 140. FIGS. 14 and 15 are views illustrating a state halfway through the main sealing process in stages. FIGS. 16A and 16B are views for describing an operation of the swaging jig movement mechanism 143m at the time of the first swaging. Furthermore, FIGS. 17, 18, and 19 are views illustrating a state halfway through the first swaging process in stages.

The main sealing/swaging processing part 140 mainly includes the pallet mounting stand 141, the main sealing jig 142, and the first swaging jig 143.

FIG. 13 illustrates a state where the transportation pallet 111 holding (placing and fixing) the semi-assembled body 40α is disposed on the pallet mounting stand 141. FIG. 13 also illustrates, in a manner similar to FIGS. 8A and 8B, a state where the semi-assembled body 40α is disposed and fixed in the assembly posture, in which the thickness direction of the sensor element 10 coincides the horizontal direction when seeing FIG. 13. The state where the transportation pallet 111 to which the semi-assembled body 40α is placed and fixed is disposed on and fixed to the pallet mounting stand 141 is also referred to simply as a state where the semi-assembled body 40α is fixed to the pallet mounting stand 141.

Although the pallet mounting stand 141 has a configuration similar to the pallet mounting stand 131 included in the tentative sealing processing part 130, it differs from the pallet mounting stand 131 in that it can be elevated in the vertical direction by the mounting stand elevating mechanism 141m. The mounting stand elevating mechanism 141m is made up of a servo cylinder.

The main sealing/swaging processing part 140 includes a support shaft 140s extending in the vertical direction in an upper position of the pallet mounting stand 141, and the main sealing jig 142 is attached to the support shaft 140s. More specifically, the support shaft 140s has a cavity part 140a which opens downward in its lower end, and the main sealing jig 142 is fixedly provided to the support shaft 140s so as to protrude to the cavity part 140a.

The main sealing jig 142 includes a substantially annular abutting part 142a, which abuts to the washer 7 which constitutes the semi-assembled body 40α from its upper side, in a lowermost end thereof in the vertical direction, and, a cavity part 142b which opens toward a vertically lower side. The main sealing jig 142 is disposed coaxially with the semi-assembled body 40α fixed to the pallet mourning stand 141.

A through hole 140b is provided in the support shaft 140s so as to extend laterally from the cavity part 140a, and the first swaging jig 143 is provided in the through hole 140b so as to be movable along an extending direction of the through hole 140b.

FIG. 13 illustrates the two through holes 140b in the horizontal direction of FIG. 13 and also illustrates the first swaging jig 143 disposed in each through hole 140b, however, the through hole 140b is actually provided in each of four sides of the cavity part 140a, that is to say, in four parts in total as described hereinafter. The first swaging jig 143 is also provided in each of the through hole 140b in the four parts (refer to FIGS. 16A and 16B).

The first swaging jig 143 includes a claw part 143a in one end directed to the cavity part 140a side and a guided part 143b which is guided by the swaging jig movement mechanism 143m in the other end side.

The swaging jig movement mechanism 143m includes a servo cylinder 144 provided to be extensible in the vertical direction and a guide member 145 provided in a lower end of the servo cylinder 144. The servo cylinder 144 and the guide member 145 are provided in four parts in total to correspond to each first swaging jig 143. The guide member 145 includes a guide surface 146 for guiding the guided part 143b of the first, swaging jig 143. The guide surface 146 is inclined at an angle of a predetermined degrees with respect to the vertical direction and is perpendicular to a vertical plane including the extending direction of the through hole 140b in which the corresponding first swaging jig 143 exists. The guided part 143b of the first swaging jig 143 is provided to be in contact with the guide surface 146 and to be movable along the inclination direction of the guide surface 146.

In performing the main sealing process and the subsequent first swaging process in the main sealing/swaging processing part 140, the transportation pallet 111, which has been delivered from the tentative sealing processing part 130 in the second delivery position Pos2 and holds laces and fixes) the semi-assembled body 40α, is disposed in the third delivery position Pos3 by the pallet movement mechanism 112, and then, the transportation pallet 111 is disposed on and fixed to the pallet mounting stand 141 in the main sealing/swaging processing part 140 together with the semi-assembled body 40α, by the pallet delivery mechanism 113, as shown in FIG. 13 (a step S31).

After the transportation pallet 111 is disposed and fixed as described above, with the operation of the mounting stand elevating mechanism 141m, the pallet mounting stand 141 to which the semi-assembled body 40α is fixed is raised as indicated by an arrow AR21 in FIG. 13. When the pallet mounting stand 141 continues to be raised, the washer 7 of the semi assembled body 40α comes to abut to the abutting part 142a of the main sealing jig 142 in due course, as shown in FIG. 14 (a step S32). At this time, the sensor element 10 is housed in the cavity part 142b.

The mounting stand elevating mechanism 141m continues to raise the pallet mounting stand 141 as indicated by an arrow AR22 in FIG. 14 after the abutting part 142a abuts to the washer 7. The abutting part 142a of the main sealing jig 142 thereby presses the washer 7 to apply a vertically downward force (load) F2 (a second force) to the washer 7 as shown in FIG. 15. At this time, the force F2 is set to be large compared with the force F1 applied at the time of the tentative sealing. The actual value of the force F2 may be set in view of an area of the abutting part 142a which abuts to the washer 7.

When the force F2 acts on the washer 7 from the abutting part 142a, the washer 7 is further pushed vertically downward, and the force F2 also acting on the powder compacts 9a and 9b via the ceramic supporters 8a and 8b acts as a compression force. The powder compacts 9a and 9b are thereby further compressed. As a result, the hermetic sealing is achieved between the measurement gas space and the reference gas space. Accordingly, the main sealing (the second compression) is achieved (a step S33).

An upper limit value of the pressure acting on the washer 7 at the time of applying the force F2 may be appropriately set in view of a material strength of the main sealing jig 142, the washer 7, or the ceramic supporter 8, for example.

Since the main sealing is performed without causing the element positioning pin 132 to abut to the sensor element 10, the sensor element 10 which is once fixed in the first position by the powder compacts 9a and 9b at the time of the tentative sealing further slightly descends at the time of the main sealing. When the protruding length of the sensor element 10 after the main sealing is defined as t2, t2 has a value closer to t0 rather than t1. The position of the sensor element 10 after the main sealing is defined as a second position. Although it is ideal to satisfy t2=t0, it can be determined that the sensor element 10 is successfully fixed as long as a value $\Delta t = t2 - t0$ falls within a predetermined error range allowed in light of characteristics desired for the gas sensor 1, that is to say, as long as the second position is within a range which is determined in advance for the position of the sensor element 10 in the assembled body 40 (the semi-assembled body 40α in this stage). Accordingly, in this preferred embodiment, the position of the element positioning pin 132 is determined so that the second position satisfies such a condition of the range. The allowable error range of $\Delta t$ may be appropriately determined in advance.

The reason why the two-stage sealing, that is, the tentative sealing of once fixing the sensor element 10 and the subsequent main sealing to achieve the hermetic sealing is performed in this preferred embodiment as described above is to prevent the occurrence of the chip or break in the sensor element 10 caused by applying a strong force at the time of the sealing. A detailed functional effect of the two-stage sealing is described hereinafter.

In some eases, there is a strong correlation (a linear relationship, for example) between the protruding length t1 after the tentative sealing and the protruding length t2 after the main sealing. In die case that such a correlation is specified in advance, the protruding length t2 of the sensor element 10 after the main sealing can be set within the allowable error range of $\Delta t$ based on the correlation, by appropriately determining the position of the lowermost end of the sensor element 10 at the time of the tentative sealing (that is to say, the upper end position of the element positioning pin 132) and the values of the forces F1 and F2 acted on by the tentative sealing jig 134 and the main sealing jig 142 at the time of the tentative sealing and the main sealing. That is to say, the sensor element 10 can be fixed in the desired position in light of the characteristics of the gas sensor 1.

After the main sealing is performed according to the above described manner, the first swaging process is subsequently performed while maintaining the state where the main sealing jig 142 is abutting to the washer 7. In outline, the first swaging is achieved by, as indicated by an arrow AR23 in FIG. 15, extending the servo cylinder 144 vertically downward in the swaging jig movement mechanism 143m.

FIGS. 16A and 16B are views for describing detailed configuration and operation of the first swaging jig 143 and the swaging jig movement mechanism 143m which is a movement mechanism of the first swaging jig 143. As illustrated by a schematic top view in a lower side of FIG. 16A, in the main sealing/swaging processing part 140, the four first swaging jigs 143 are provided toward four directions in the horizontal plane, respectively. Each first swaging jig 143 is configured to he movable along the through hole 140b extending in the horizontal direction. Under the state that the washer 7 of the semi-assembled body 40α abuts to the main sealing jig 142, these four first swaging jigs 143 are symmetrically located with respect to the inner tube 6 of the semi-assembled body 40α.

In the swaging jig movement mechanism 143m, when the servo cylinder 144 corresponding to each first swaging jig 143 is extended vertically downward as indicated by the arrow AR24, the guide member 145 associated with the servo cylinder 144 descends vertically downward. The guide member 145 then applies a vertically downward force to the guided part 143b of the first swaging jig 143 which is in contact with the guide surface 146 of the guide member 145 and is about to press down the guided part 143b. However, as described above, although the guided part 143b is provided to be movable along the inclination direction of the guide surface 146 which is the inclination surface, the first swaging jig 143 as a whole is configured to be movable along the through hole 140b extending in the horizontal direction. That is to say, the moving direction of the first swaging jig 143 is limited within the horizontal plane. Accordingly, as a result, when the guide member 145 descends due to the extension of the servo cylinder 144, the guided part 143b is relatively raised along the guide surface 146 as indicated by an arrow AR25 in FIG. 16A and at the same time, the first swaging jig 143 moves in the through hole 140b toward the inner tube 6 as indicated by an arrow AR26. When the servo cylinder 144 extends by a predetermined distance $\Delta Z$, the claw part 143a of the first swaging jig 143 comes to abut to an outer periphery surface of the inner tube 6.

As shown in FIGS. 16A and 16B, an end of the claw part 143a included in each first swaging jig 143 has a curved surface in accordance with a shape of the inner tube 6, so that when the claw part 143a abuts to the inner tube 6, its whole curved surface is abutted to the inner tube 6.

As shown in FIG. 16B, a position (a height position) in which each claw part 143a abuts to the outer periphery surface of the inner tube 6 is set to a position right above the washer 7. In the manufacturing apparatus 100 according to this preferred embodiment, determined are the second force F2 added to the washer 7 in the main sealing process and the configuration and operation manner of the swaging jig movement mechanism 143m including the shape of the claw part 143a of the first swaging jig 143 or the like, in order to satisfy the positional relationship.

As shown in FIG. 17, when the servo cylinder 144 is continuously extended vertically downward as indicated by, an arrow AR 27 after the claw part 143a of the first swaging jig 143 comes to abut to the outer periphery surface of the inner tube 6, the inner tube 6 is pressed by the claw part 143a. The inner tube 6 is thereby swaged from the outer periphery side, and as shown in FIG. 18, the concave portion 6a is formed in the outer periphery surface of the inner tube 6 located right above the washer 7 (a step S41). The annularly-mounted member in the tubular body 30 is thereby completely constrained. Since the first swaging jigs 143 are located only in the four sides as shown in FIGS. 16A and 16B, the concave portion 6a is not necessarily formed around the inner tube 6 in the whole circumferential direction uniformly and continuously.

After the concave portion 6a is formed, the servo cylinder 144 is shortened vertically upward as indicated by an arrow AR28 in FIG. 18. Accordingly, the first swaging jig 143 which has pressed the inner tube 6 is also taken off as indicated by an arrow AR29 (a step S42).

After the first swaging jig 143 is taken off, the mounting stand elevating mechanism 141m operates again to lower the pallet mounting stand 141 to a default position as indicated by an arrow AR30 (a step S43). FIG. 19 illustrates a state after the pallet mounting stand 141 descends to the default position.

Then, the transportation pallet 111 holding the semi-assembled body 40α on which the first swaging has been performed is delivered from the pallet mounting stand 141 to the pallet movement mechanism 112 by the pallet deliver mechanism 113 (a step S44). That is to say, the transportation pallet 111 is disposed in the third deliver position Pos3 again. The main sealing process and the subsequent first swaging process are thereby finished.

<Second Swaging (Retightening)>

The semi-assembled body 40α on which the main sealing and the first swaging are performed in the main sealing swaging processing part 140 is provided to the second swaging (retightening) process performed in the retightening processing part 150 (the step S5 in FIG. 3). The second swaging process is a process for further securing the constraining, of the annularly-mounted member in the tubular body 30.

Figure 20:
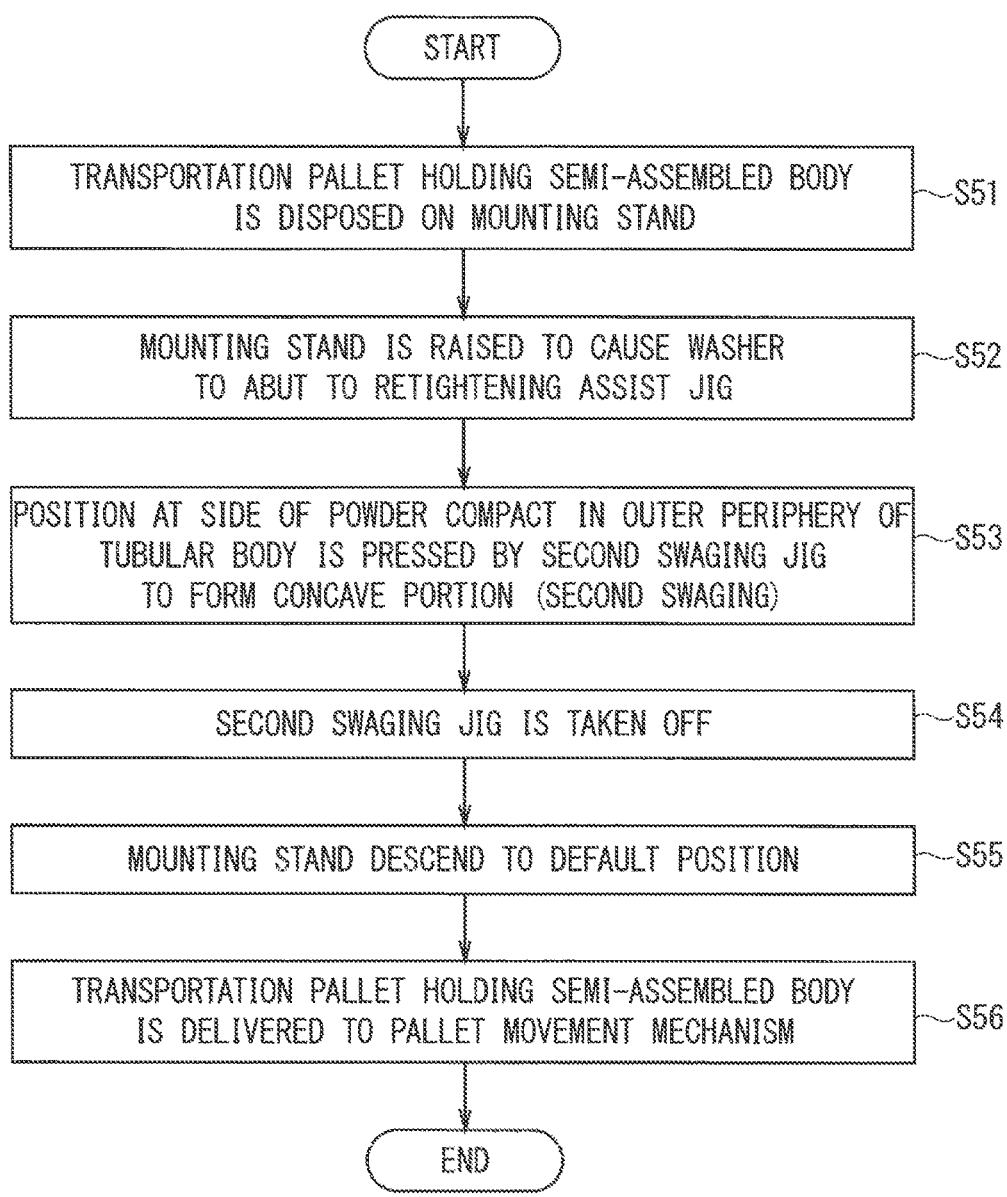
FIG. 20 is a view illustrating a more specific procedure of a second swaging process.
Figure 21:
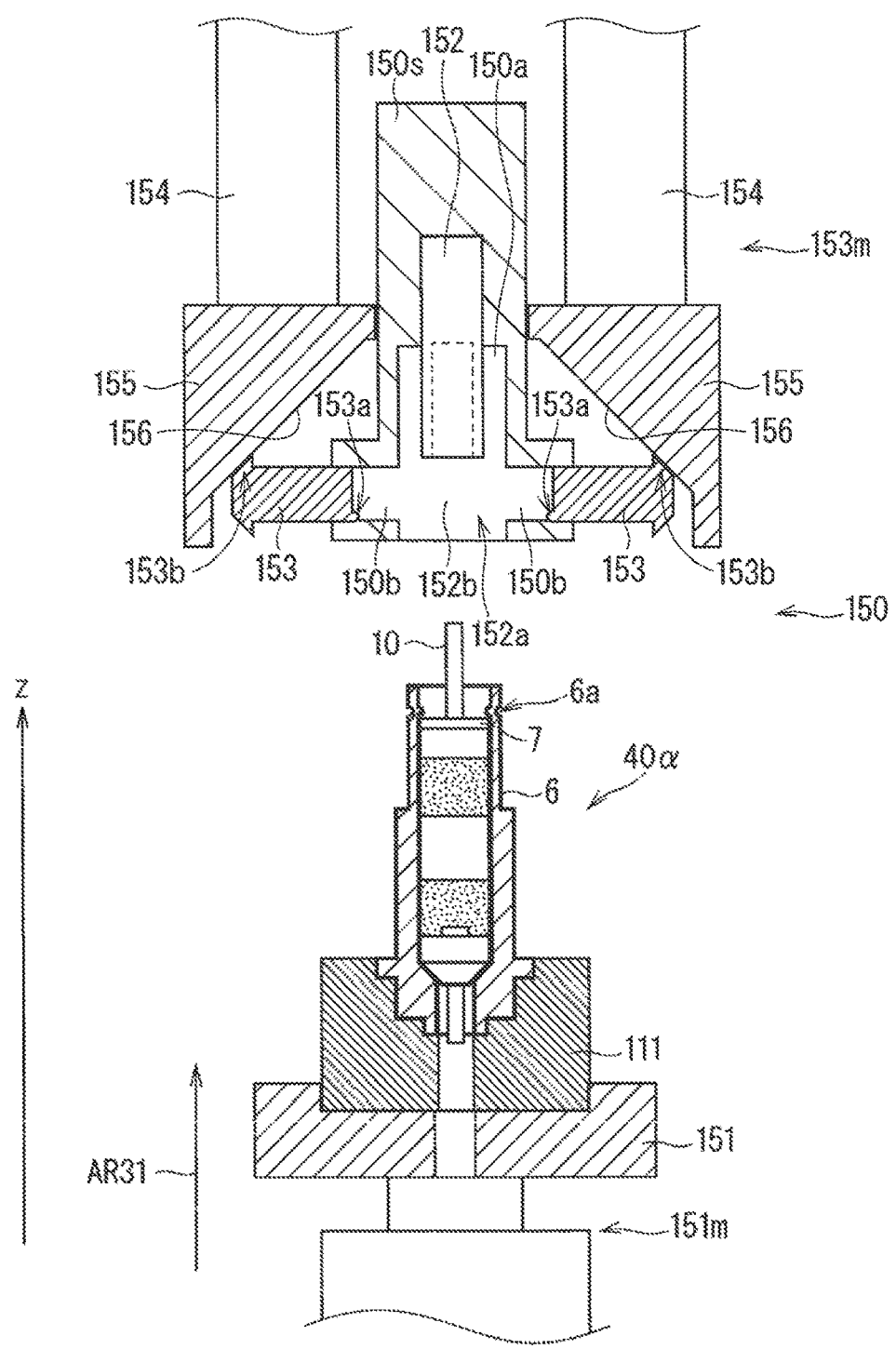
FIG. 21 is a side view schematically illustrating a structure of a retightening processing part 150.

FIG. 20 is a view illustrating a more specific procedure of the second swaging process. FIG. 21 is a side view (a partial cross sectional view) schematically illustrating a structure of the retightening processing part 150. Furthermore, FIGS. 22, 23, 24, and 25 are views illustrating a state halfway through the second swaging process in stages.

The retightening processing part 150 mainly includes the pallet mounting stand 151, the retightening assist jig 152, and the second swaging jig 153.

FIG. 21 illustrates a state where the transportation pallet 111 holding (placing and fixing) the semi-assembled body 40α is disposed on the pallet mounting stand 151. FIG. 21 also illustrates, in a manner similar to FIGS. 8A and 8B, a state where the semi-assembled body 40α is disposed and fixed in the assembly posture, in which the thickness direction of the sensor element 10 coincides to the horizontal direction when seeing FIG. 21. The state where the transportation pallet 111 to which the semi-assembled body 40α is placed and fixed is disposed on and fixed to the pallet mounting stand 151 is also referred to simply as a state where the semi-assembled body 40α is fixed to the pallet mounting stand 151.

The retightening processing part 150 has a configuration similar to the main sealing/swaging processing part 140 described above. That is to say, the pallet mounting stand 151 and the mounting stand elevating mechanism 151m have configurations similar to the pallet mounting, stand 141 and the mounting stand elevating mechanism 141m of the main sealing/swaging processing part 140. The retightening processing part 150 includes a support shaft 150s extending in the vertical direction in an upper position of the pallet mounting stand 151, and the support shaft 150s has a cavity part 150a which opens downward in its lower end. The retightening assist jig 152 is fixedly provided to the support shaft 150s so as to protrude to the cavity part 150a. These configurations are similar to the configuration manner of the support shaft 140s, the cavity part 140a, and the main sealing jig 142 in the main sealing/swaging processing part 140.

However, a height position of an abutting part 152a of the retightening assist jig 152 is determined so that a height position of the powder compact 9a constituting the semi-assembled body 40α coincides with a height position of a claw part 153a of the second swaging jig 153 under a state that the washer 7 abuts to the abutting part 152a. A protruding length of the retightening assist jig 152 protruding from the support shaft 150s is thereby smaller than that of the main sealing jig 142 protruding from the support shaft 140s.

The configurations of the second swaging jig 153 (the claw part 153a and a guided part 153b), a through hole 150b in which the second swaging jig 153 is disposed, and the swaging jig movement mechanism 153m for moving the second swaging jig 153 in the horizontal plane (a servo cylinder 154, a guide member 155, and the guide surface 156) are also substantially similar to those of the first swaging jig 143 (the claw part 143a and the guided part 143b), a through bole 140b in which the first swaging jig 143 is disposed, and the swaging jig movement mechanism 143m for moving the first swaging jig 143 in the horizontal plane (the servo cylinder 144, the guide member 145, and the guide surface 146) Accordingly, a detailed description of the configuration in the retightening processing part 150 is omitted.

However, the shape of the claw part 153a of the second swaging jig 153 may differ from the shape of the claw part 143a of the first swaging jig 143. The shape of the claw part 153a of the second swaging jig 153 illustrated in FIGS. 21 to 25 differs from the shape of the claw part 143a of the first swaging jig 143 illustrated in FIGS. 13 to 19.

In performing the second, swaging (retightening) process in the retightening processing part 150 having the above configuration, firstly, the transportation pallet 111, which has been delivered from the main sealing/swaging processing part 140 in the third delivery position Pos3 and holds (places and fixes) the semi-assembled body 40α, is disposed in the fourth delivery position Pos4 by the pallet movement mechanism 112, and then, the transportation pallet 111 is disposed on and fixed to the pallet mounting stand 151 in the retightening processing part 150 together with the semi-assembled body 40α, by the pallet delivery mechanism 113, as shown in FIG. 21 (a step S51).

Figure 22:
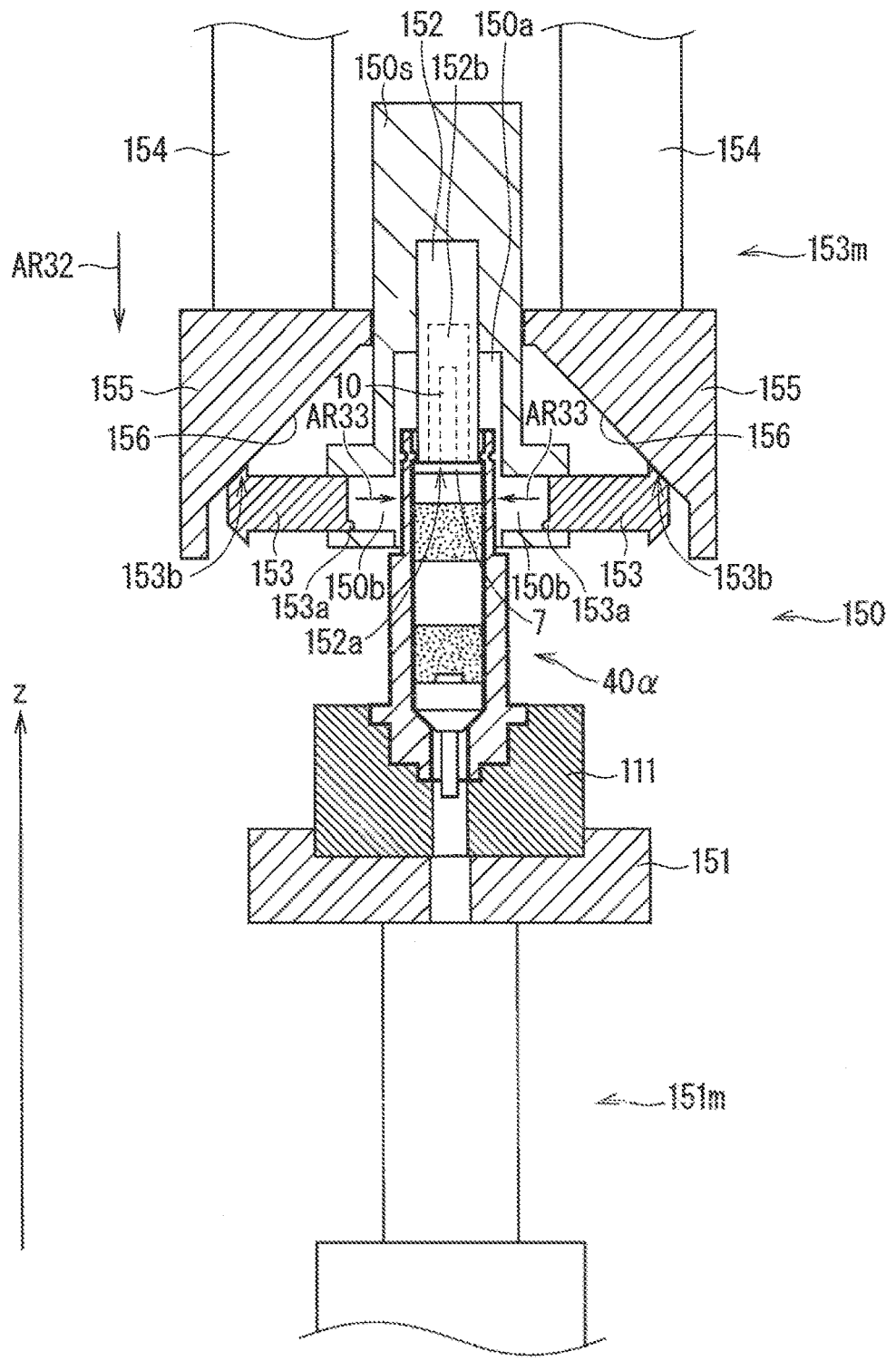
FIG. 22 is a view illustrating a state halfway through the second swaging process in stages.

After the transportation pallet 111 is disposed and fixed as described above, with the operation of the mounting stand elevating mechanism 151m, the pallet mounting stand 151 to which the semi-assembled body 40α is fixed is raised as indicated by an arrow AR31 in FIG. 21. When the pallet mounting stand 151 continues to be raised, the washer 7 of the semi-assembled body 40α comes to abut to the abutting part 152a of the retightening, assist jig 152 in due course as shown in FIG. 22 (a step S52). At this time, the sensor element 10 is housed in the cavity part 152b.

Figure 23:
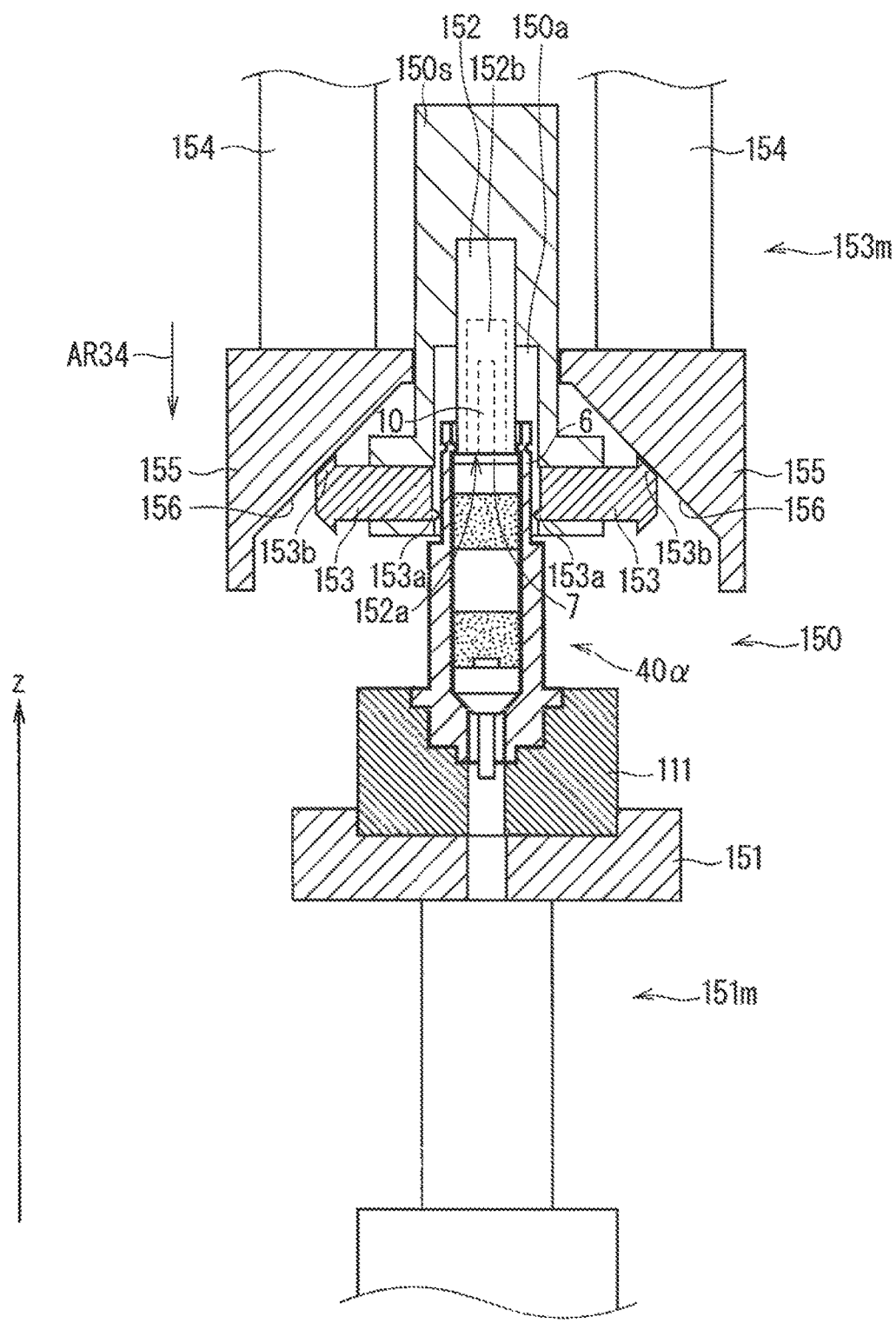
FIG. 23 is a view illustrating a state halfway through the second swaging process in stages.

After the washer 7 abuts to the abutting part 152a according to the above described manner, the servo cylinder 154 is extended vertically downward in the swaging jig movement mechanism 153m as indicated by an arrow AR32 in FIG. 22. Then, the second swaging jig 153 moves in the through hole 150b toward the inner tube 6 as indicated by an arrow AR33, and the claw pan 153a of the second swaging jig 153 comes to abut to the outer periphery surface of the inner tube 6 in the lateral position of the powder compact 9a in due course as shown in FIG. 23.

When the servo cylinder 154 is continuously extended vertically downward, as indicated by an arrow AR34, after the claw part 153a comes to abut to the outer periphery surface of the inner tube 6, the inner tube 6 is pressed by the claw part 153a. The inner tube 6 is thereby swaged from the outer periphery side, and as shown in FIG. 24, the concave portion 8b is formed in the outer periphery surface of the inner tube 6 in the lateral position of the powder compact 9a (a step S53). The constraining of the annularly-mounted member in the tubular body 30 is further secured as a result that the concave portion 6b is formed. The assembly of the assembled body 40 is finished by forming the concave portion 6b.

After the concave portion 6b is formed, the servo cylinder 154 is shortened vertically upward as indicated by an arrow AR35 in FIG. 24. Accordingly, the second swaging jig 153 which has pressed the inner tube 6 is also taken off as indicated by an arrow AR36 (a step S54).

After the second swaging jig 153 is taken off, the mounting stand elevating mechanism 151m operates again to lower the pallet mounting stand 151 to a default position as indicated by an arrow AR 37 (a step S55), FIG. 25 illustrates a state after the pallet mounting stand 141 descends to the default position, Then, the transportation pallet 111 holding the assembled body 40 is delivered from, the pallet mounting stand 151 to the pallet movement mechanism 112 by the pallet deliver mechanism 113 (a step S56). That is to say, the transportation pallet 111 is disposed in the fourth deliver position Pos4 again. The second swaging (retightening) process is thereby finished. Subsequently, the assembled body 40 is delivered to the assembled body standby pan 170 to be provided to the process in the subsequent stages.

<Effect of Two-Stage Sealing>

Figure 26:
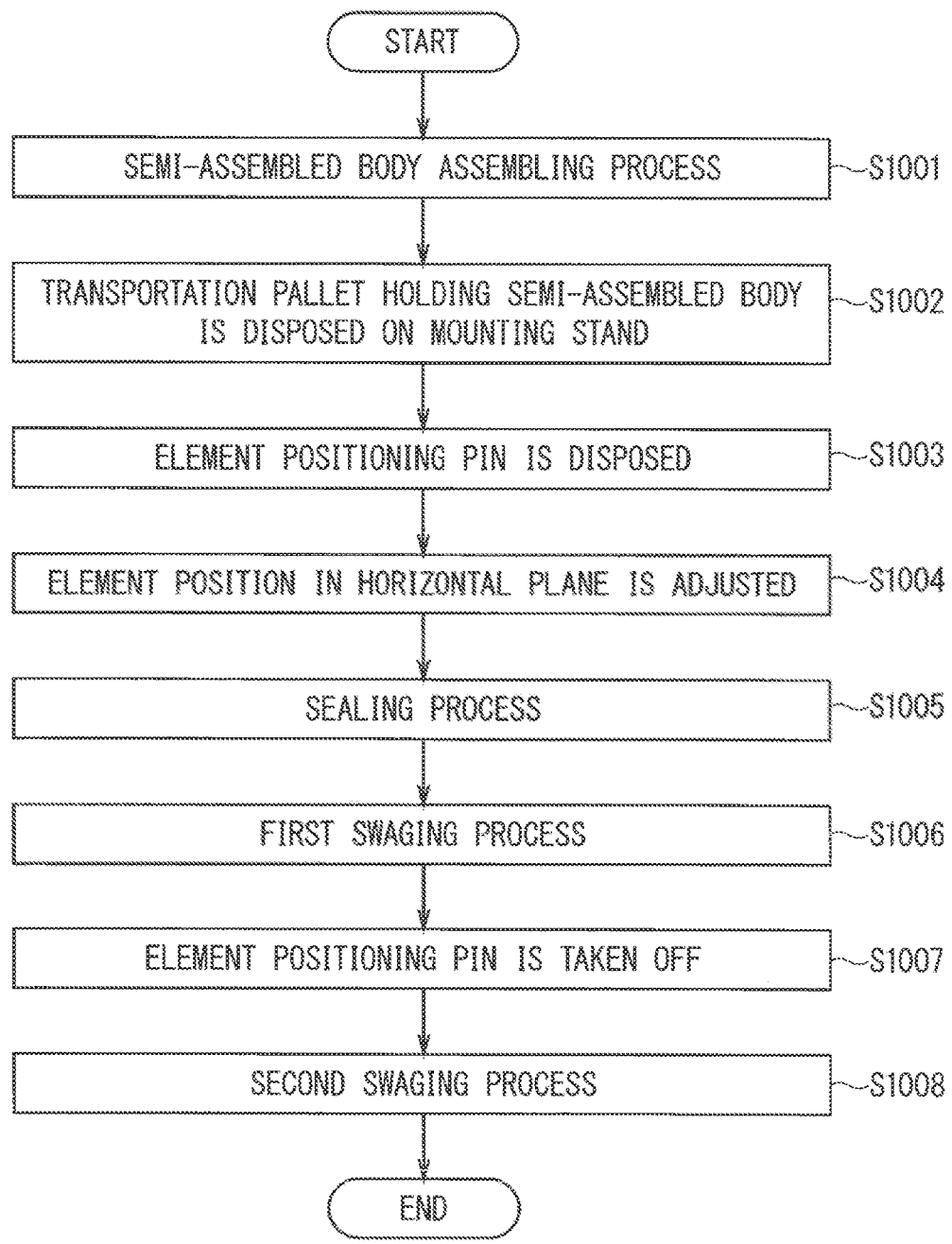
FIG. 26 is a view illustrating a procedure of a hermetic sealing in a comparison example.

Next, the effect of the two-stage sealing performed according to the above described manner is explained by comparison with a case of performing a sealing only in one stage (referred to as the comparison example hereinafter). FIG. 26 is a view illustrating a procedure of a hermetic sealing in a comparison example.

In the procedure in the comparison example, steps S1001 to S1004 are the same as the step S1 and the steps S21 to S23, which are the part of the step S2, in the case of the two-stage sealing according to this preferred embodiment shown in FIG. 3 or FIG. 7.

However, they differ from each other in the subsequent process. In the case of the comparison example, the sealing process for airtightness is performed as early as in a stage in which the tentative sealing is performed in the case of the two-stage sealing (a step S1005). Furthermore, the sealing process is performed without taking off the element positioning pin. After performing the first swaging process (a step S1006) following the sealing process, the element positioning pin is taken off (a step S1007), and finally, the second swaging process is performed in a manner similar to the case of the two-stage sealing (a step S1008).

Figure 27A:
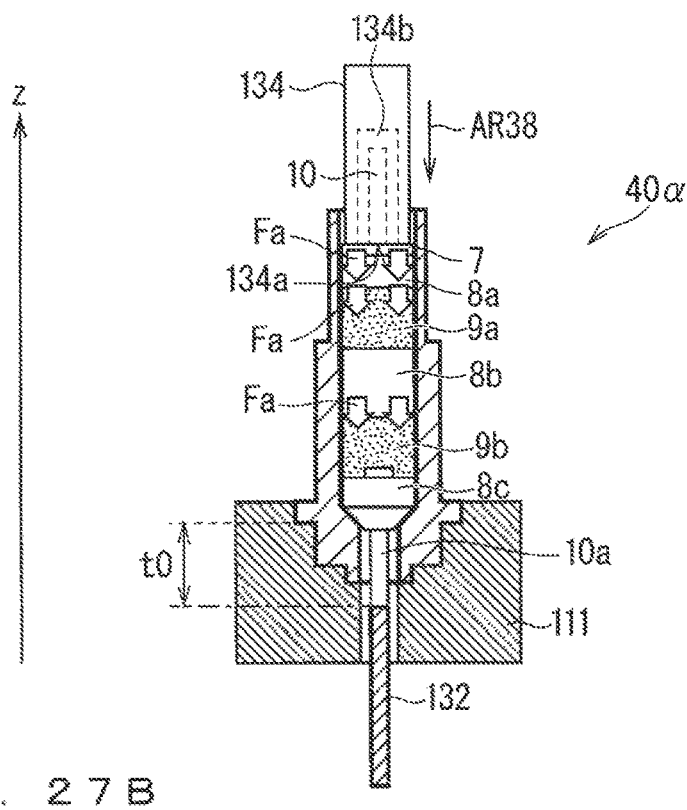
FIGS. 27A and 27B are typical cross-sectional views illustrating the sealing in the comparison example and its partial enlarged view.
Figure 27B:
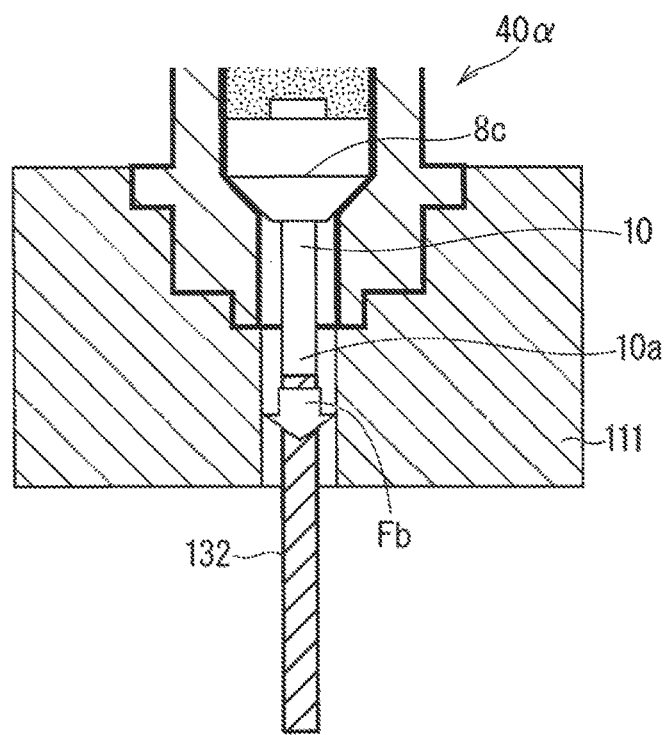

FIGS. 27A and 27B are typical cross-sectional views illustrating the sealing in the comparison example and its partial enlarged view. Since the sealing in the comparison example is performed in a processing part having a configuration similar to the tentative sealing processing part 130 in this preferred embodiment, the sealing is described hereinafter using the constituent element of the tentative sealing processing part 130 for convenience. However, the pallet mounting stand 131 in which the transportation pallet 111 is disposed is omitted in FIGS. 27A and 27B. The tentative sealing jig 134 is also referred to simply as the sealing jig 134 in the description hereinafter.

As, shown in FIG. 27A, the sealing in the comparison example is achieved by the sealing jig elevating mechanism 134m, not shown, causing the sealing jig 134 to abut to the washer 7 from the upper side of the semi-assembled body 40α toward the vertically lower side as indicated by an arrow AR38, in the state where the sensor element 10 abuts to the element positioning pin 132. The reason why the sealing in the comparison example is performed under the state that the sensor element 10 abuts to the element positioning pin 132 without taking off the element positioning pin 132 is that, since the sealing is performed without positioning the sensor element 10 in advance, sensor element 10 needs to be positioned together with the sealing. The element positioning pin 132 is disposed so that the protruding length of the sensor element 10 is set to t0 as shown in FIG. 27A for purpose of performing the positioning described above.

The force Fa which the sealing jig 134 applies to the washer 7 at the time of the sealing in the comparison example needs to be nearly equal to the force F2 applied at the time of the main sealing, in order to achieve the hermetic sealing similar to the main sealing in the two-stage sealing described above. When such a force Fa acts on the washer 7, the force Fa also acting on the powder compacts 9a and 9b via the ceramic supporters 8a and 8b acts as the compression force. Accordingly, the powder compacts 9a and 9b are compressed, and as a result, the hermetic sealing is performed between the measurement gas space and the reference gas space.

In the case of the comparison example, however, since the lowermost end of the sensor element 18 is in contact with the element positioning pin 132, a force Fb which is nearly equal to the force Fa also acts on the first tip portion 10a of the sensor element 10 as shown in FIG. 27B. Since a cross section of the sensor element 10 perpendicular to the longitudinal direction is smaller than a cross section of the annularly-mounted members such as the washer 7, the pressure acting on the first tip portion 10a is larger than the pressure acting on the annularly-mounted members. Accordingly, in the case of the comparison example, a strength of the sensor element 10 may not withstand the force Fb, and a defect of chip or break may thereby occur in the sensor element 10.

In contrast, in the case of the two-stage sealing performed in this preferred embodiment, the lowermost end of the sensor element 10 abuts to the element positioning pin 134 at the time of the tentative sealing, however, the force F1 added to compress the powder compact at the time of the tentative sealing is sufficiently smaller than the force F2 added at the time of the main sealing for securing the airtightness. Since the lowermost end of the sensor element 10 does not abut to the element positioning pin 134 at the time of the main sealing, differing from the case of the comparison example, the strong force does not act on the first tip portion 10a of the sensor element 10 at the time of the hermetic sealing. Accordingly, in the case of the two-stage sealing performed in this preferred embodiment, the chip or break does not occur in the sensor element 10. In this preferred embodiment, accordingly, the occurrence of the defect caused by the chip or break in the sensor element 10 can be reliably prevented at the time of the hermetic sealing of the assembled body 40.

Furthermore, the sensor element can be appropriately fixed in the desired position by appropriately determining a position of the element positioning pin at the time of the tentative sealing, the force F1 acting on the powder compact at the time of the tentative sealing, and the force F2 acting on the powder compact at the time of the main sealing.

As described above, according to this preferred embodiment, the process of, during assembling the gas sensor, positioning and fixing the sensor element and hermetically sealing the space of both end sides of the sensor element by compressing the powder compact is performed in the two stages, that is, the tentative sealing (the first compression) mainly for purpose of positioning the sensor element and the main sealing (the second compression) performed after the tentative sealing, without using the element positioning pin, so that fixing of the sensor element without the chip or break therein as well as hermetic sealing is achieved inside the tubular body.

The position of the element positioning pin is determined in consideration of the positional deviation of the sensor element at the time of the main sealing, so that fixing of the sensor element in a desired position without the chip or break therein as well as hermetic sealing is achieved inside the tubular body.

EXAMPLE

Example 1

In order to evaluate a force (a load) needed to achieve the hermetic sealing at the time of the main sealing, prepared were a plurality of semi-assembled bodies 40α in which a size, of a cross section of the sensor element 10 perpendicular to the longitudinal direction is 4.25 mm×1.45 mm and external diameters of the washer 7, ceramic supporters 8a, 8b, and 8c, and powder compacts 9 (9a and 9b) are 8.9 mm, 8.85 mm, 8.7 mm, 8.7 mm, and 8.9 mm, respectively, and the sealing was performed on each semi-assembled body 40α under a different condition to manufacture five types of assembled bodies for evaluation. Then, a leak test was performed for each assembled body.

The assembled bodies were manufactured by a procedure similar to the comparison example shown in FIG. 26 except for not using the element positioning pin 132. The reason why the element positioning pin 132 is not used and the tentative sealing is not performed is that it is considered that the position to which the sensor element 10 is fixed is not influenced by a leak amount in so far as the fixing is performed using the powder compacts 9.

The load which the (tentative) sealing jig 134 applied to the washer 7 at the time of the sealing was varied in five levels, that is, 450 kgf (4412.99N), 500 kgf (4903.33N), 550 kgf (5393.66N), 600 kgf (5883.99N), and 650 kgf (6374.32N). At that time, the (tentative) sealing jig 134 whose abutting part 134a had an inner diameter of 6.2 mm and an outer diameter of 7.7 mm was used.

Figure 28:
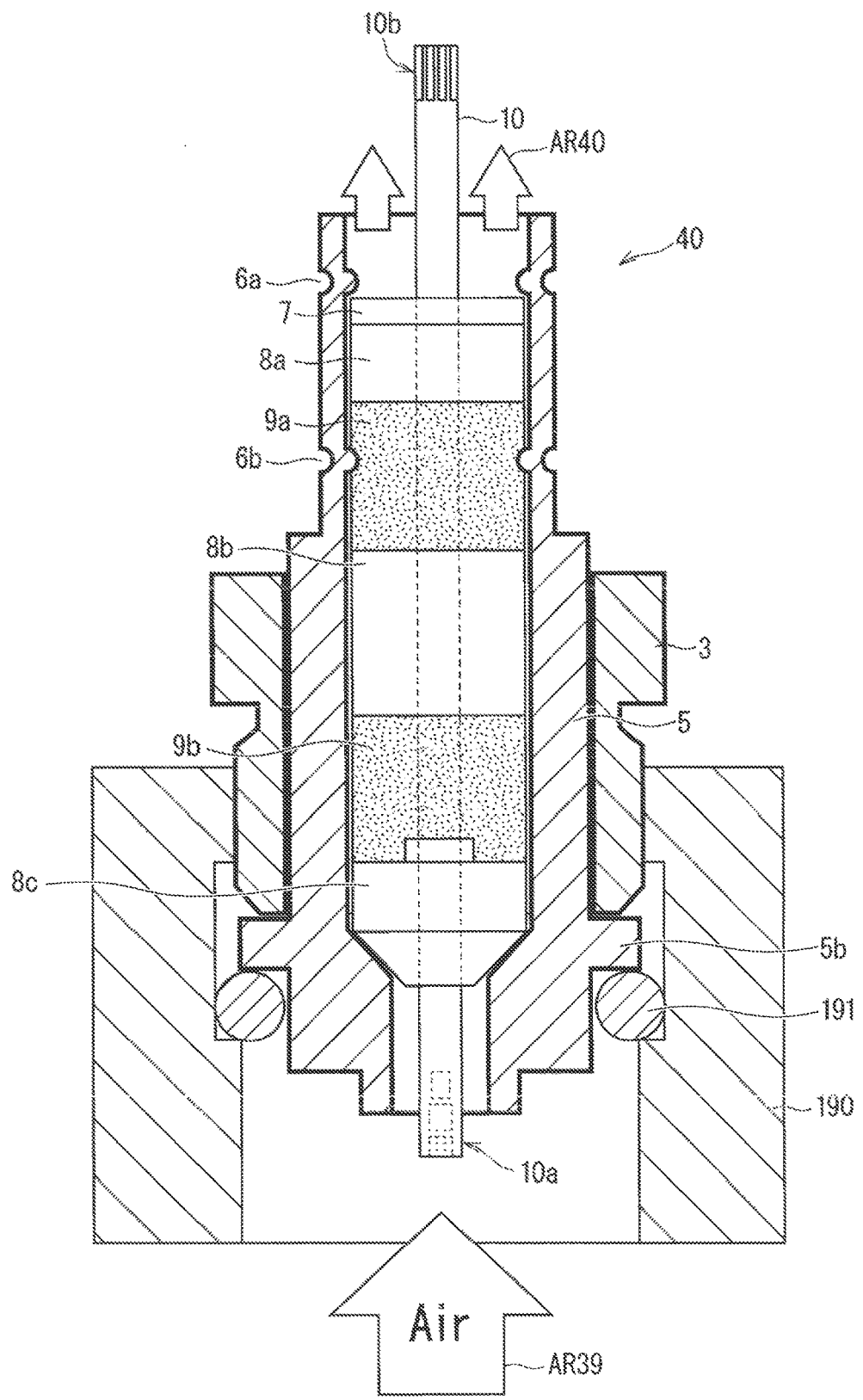
FIG. 28 is a view schematically illustrating a leak test.

FIG. 28 is a view schematically illustrating the leak test. The leak test was performed, as shown in FIG. 28, under a circumstance that the assembled body was fixed to the test fixing stand 190 in such a posture that the first tip portion 10a side of the sensor element 10 was located in the vertically lower side, with screwing the fixing bolt 3 attached to the assembled body for evaluation to a test fixing stand 190. Air was made to flow from a lower side of the test fixing stand 190 as indicated by an arrow AR39, so that a flow rate of the air near the second tip portion 10b flowing from the inside of the assembled body for evaluation as indicated by an arrow AR40 was obtained as a leak amount.

The test fixing stand 190 includes a sealing rubber 191 to perform a sealing between the flange portion 5b of the housing 5 and the test fixing stand 190 at the time when the fixing bolt 3 is screwed into the test fixing stand 190. Accordingly, there is a flow path of the air only inside the assembled body at the time of the leak test.

The pressure of the air flowing at the time of the leak test was set to 0.4 MPa, and it was determined that the hermetic sealing was successfully achieved when the leak amount was 0.10 cm$^3$/min. or less. This threshold value of 0.10 cm$^3$/min. is an upper limit value of the leak amount of the measurement gas leaked inside the gas sensor 1. Even when the measurement gas is leaked inside the gas sensor 1, the leakage does not influence the concentration measurement of the gas component as long as the leak amount is equal to or smaller than the above value.

Figure 29:
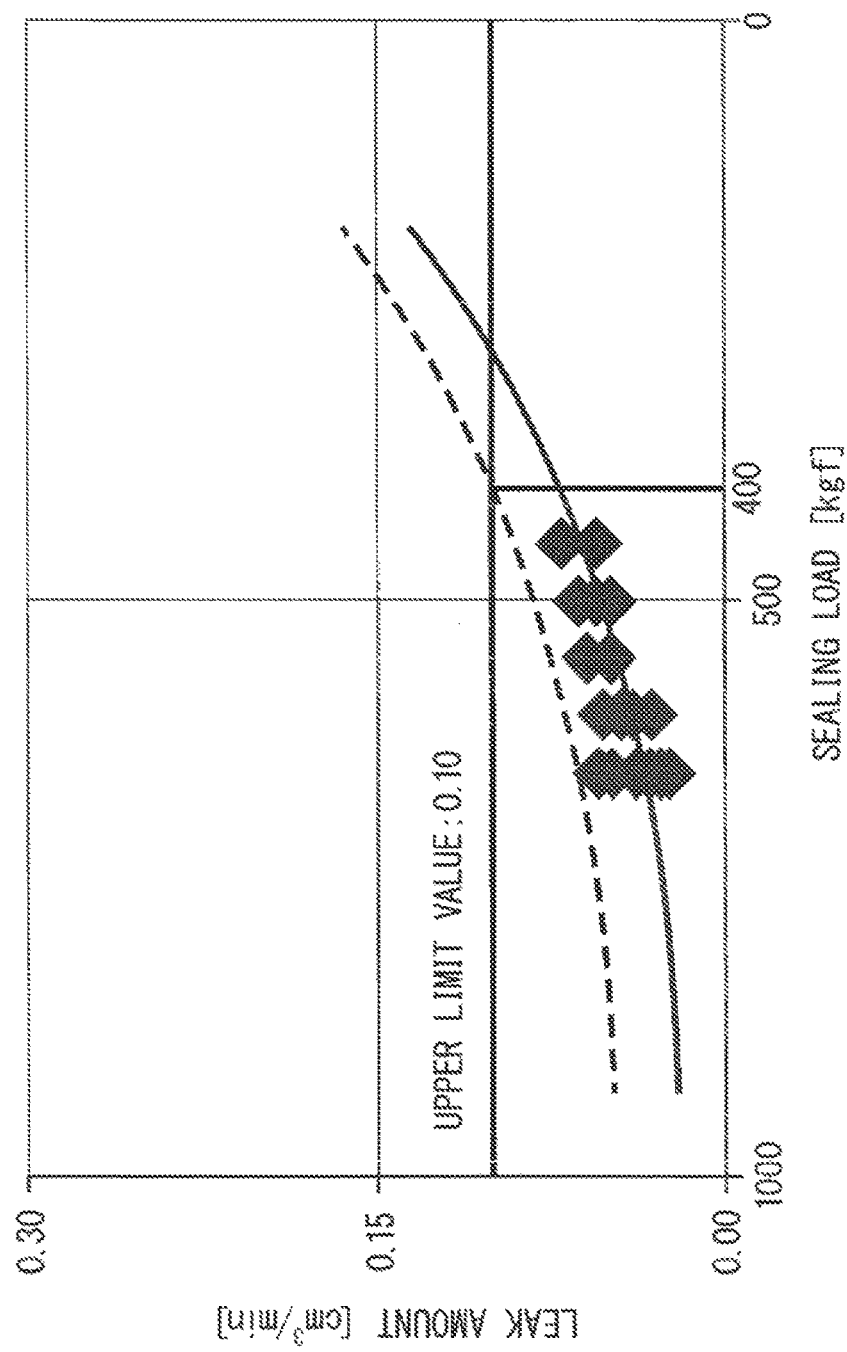
FIG. 29 is a view illustrating a relationship between a sealing load and a leak amount of air in the leak test.

FIG. 29 is a view illustrating a relationship between a sealing load and a leak amount of the air in the leak test performed under the condition described above. It is expected from FIG. 29 that the leak amount is equal to or smaller than 0.10 cm³/min. when the sealing load is 400 kgf (3922.66N) or larger, even in the consideration of the variation.

Example 2

In order to confirm the effectiveness of the tentative sealing, the evaluation of the load needed to fix the sensor element 10 using the powder compact 9 and the load which causes the occurrence of the chip in the sensor element 10 was performed on the semi-assembled body 40α manufactured under the same condition as that used in the Example 1.

Specifically, the step S1 and the steps S21 to S24 which are the part of the step S2 in the manufacturing procedure of the assembled body were performed with varying the sealing load in eight levels, and the evaluated are whether or not the sensor element 10 was fixed and a frequency of occurrence of the chip in each level. The sealing loads in each level are set to 5 kgf (49.033N), 10 kgf (98.067N), 20 kgf (196.133N), 40 kgf (392.266N), 80 kgf (784.53N), 100 kgf (980.665N), 180 kgf (1765.20N), and 300 kgf (2942.00N), respectively, The evaluation is performed on the five semi-assembled body 40α for each level. The (tentative) sealing jig 134 used in the working example 2 was the same as that of the working example 1. A cylindrical member with a diameter of 1.5 mm was used as the element positioning pin 132 and is disposed so that the protruding length t1 was set to 15 mm.

Listed in a table 1 are the sealing load in each level, whether or not the sensor element 10 was fixed, and a frequency of occurrence of the chip in the sensor element 10. In this Example, the sensor element 10 is determined to be fixed as long as the protruding length t1 of 15 mm is maintained, and "OK" is described in the table 1. In contrast, the sensor element 10 is determined to be not fixed when the protruding length t1 of 15 mm is not maintained, and "NG" is described in the table 1.

TABLE 1

| SEALING LOAD (kgf) | FIXING OF SENSOR ELEMENT | FREQUENCY OF OCCURRENCE OF CHIP |
|---|---|---|
| 5 | NG | CANNOT BE EVALUATED |
| 10 | OK | 0/5 |
| 20 | OK | 0/5 |
| 40 | OK | 0/5 |
| 80 | OK | 0/5 |
| 100 | OK | 2/5 |
| 180 | OK | 2/5 |
| 300 | OK | 3/5 |

As, shown in the table 1, the sensor element 10 was appropriately fixed when, the sealing load is equal to or larger than 10 kgf (98.067N). In contrast, the sensor element 10 was not fixed when the sealing load is 5 kgf (49.033N), so that the occurrence of the chip cannot be evaluated when the sealing load is 5 kgf (49.033N).

In the meanwhile, with regard to the frequency of occurrence of the chip, the chip does not occur when the sealing load falls within a range of 10 kgf (98.067N) to 80 kgf (784.53N), however, the chip occurs when the sealing load is equal to or larger than 100 kgf (980.665N).

The above result indicates that the sensor element 10 can be fixed without the occurrence of chip when the sealing load falls within the range of 10 kgf (98.067N) to 80 kgf (784.53N).

Example 3

In this Example, a correlation between the protruding length t1 after the tentative sealing and the protruding length t2 after the main sealing is evaluated.

Specifically, the assembled body for evaluation was manufactured by the procedure shown in FIG. 3 with varying the protruding length t1 at the time of the tentative sealing (that is to say, the position of the element positioning 132) and the sealing load at the time of the tentative sealing and main sealing, and the protruding length t2 after the main sealing is evaluated.

FIG. 30 is a view plotting the protruding length t2 after the main sealing with respect to the protruding length t1 at the time of the tentative scaling. As shown in FIG. 30, each data point is linearly distributed. When a regression line is obtained based on the distribution, a relational expression of $$t2 = 1.0358 t1 + 1.3174 \quad (1)$$

is obtained, and the following value is obtained with regard to a correlation coefficient R.

$$R^2 = 0.997 \quad (2)$$

That is to say, it is confirmed that there is a strong correlation (a linear relationship) between the protruding length t2 after the main sealing and the protruding length t1 at the time of the tentative sealing. This result indicates that the protruding length t2 after the main sealing can be controlled by controlling the protruding length t1 at the time of the tentative sealing.

The invention claimed is:

1. A method for manufacturing a gas sensor, said method comprising:

a step of obtaining an assembled body constituting said gas sensor by performing a predetermined processing on a semi-assembled body which is manufactured in advance, wherein said semi-assembled body comprises: an annular-mounted assembly in which a plurality of annularly-mounted members each having a disc shape or cylindrical shape are annularly mounted around a sensor element with an elongated plate shape comprising a ceramic, the plurality of annularly-mounted members including at least a first ceramic powder compact located on one end side of said sensor element and a second ceramic powder compact located on an other end side of said sensor element opposite said one end side of said sensor element; and a tubular body which is annularly mounted to an outer periphery of said, annularly-mounted members and capable of engaging one end side of said annularly, mounted members therein, and said step of obtaining said assembled body comprising steps of:

a) causing said one end side of said sensor element constituting said semi-assembled body to abut to a predetermined positioning member for positioning said sensor element;

b) applying a first force to said annularly-mounted members from said other end side of said sensor element having been positioned through said step a) and thereby compressing said first powder compact and said second powder compact so as to fix said sensor element inside of said tubular body; and c) after said step b), applying a second force which is larger than said first force to said annularly-mounted members from said other end side of said sensor element with said one end side of said sensor element not abutting to any positioning member including said positioning member such that a position of said sensor element is not fixed when applying the second force and thereby further compressing said first powder compact and said second powder compact so as to hermetically seal between spaces located on said one end side and said other end side of said sensor element inside of said tubular body.

2. The method for manufacturing said as sensor according to claim 1, wherein
a posture of said semi-assembled body in which a longitudinal direction of said sensor element extends in a vertical direction and said other end side is located in an upper side is defined as an assembly posture of said semi-assembled body,
said step a) is a step of causing said positioning member to abut to said one end side of said sensor element from a lower side of said sensor element with said semi-assembled body being in said assembly posture,
in said step b), said first force is applied to an upper portion of said annularly-mounted members as a vertically downward force under a state that said semi-assembled body is in said assembly posture and said sensor element has been positioned through said step a), so that, said first powder compact and said second powder compact are compressed, and said sensor element is fixed in a first position depending on a position of said positioning member by said compressed powder compact, and
in said step c), said second force is applied to said upper portion of said annularly-mounted members in said state where said semi-assembled body is in said assembly posture.

3. The method for manufacturing said gas sensor according to claim 2, wherein
said sensor element is displaced from said first position to a second position in a vertical direction through said step c), and
said positioning member is disposed in said step a) so that said second position is located within a predetermined range which is determined in advance as a position of said sensor element in said assembled body.

4. The method for manufacturing said gas sensor according to claim 3, wherein
in said step a), said positioning member is disposed so that said second position is located within said predetermined range which is determined based on a correlation between said first position and said second position of said sensor element, said correlation being specified in advance.

5. The method for manufacturing said gas sensor according to claim 4,
said step of obtaining said assembled body further comprising a step of:
d) swaging said tubular body, in said state where said semi-assembled body is in said assembly posture, with a first swaging element from an outer periphery thereof, in a first swaging position which is located above an uppermost portion of said annularly-mounted members whose said first powder compact and said second powder compact has been compressed in said step c).

6. The method for manufacturing said gas sensor according to claim 3,
said step of obtaining said assembled body further comprising a step of:
d) swaging said tubular body, in said state where said semi-assembled body is in said assembly posture, with a first swaging element from an outer periphery thereof, in a first swaging position which is located above an uppermost portion of said annularly-mounted members whose said first powder compact and said second powder compact has been compressed in said step c).

7. The method for manufacturing said gas sensor according to claim 2,
said step of obtaining said assembled body further comprising a step of:
d) swaging said tubular body, in said state where said semi-assembled body is in said assembly posture, with a first swaging element from an outer periphery thereof, in a first swaging position which is located above an uppermost portion of said annularly-mounted members whose said first powder compact and said second powder compact has been compressed in said step c).

8. The method for manufacturing said gas sensor according to claim 7, wherein
said step d) is successively performed subsequent to said step c) with said second force being kept to apply to said upper portion of said annularly-mounted members.

9. The method for manufacturing said gas sensor according to claim 8,
said step of obtaining said assembled body further comprising a step of:
e) swaging said tubular body, in said state where said semi-assembled body is in said assembly posture, with a second swaging element from an outer periphery thereof, in a second swaging position which is located in a lateral position of said second powder compact after said step d).

10. The method for manufacturing said gas sensor according to claim 7,
said step of obtaining said assembled body further comprising a step of:
e) swaging said tubular body, in said state where said semi-assembled body is in said assembly posture, with a second swaging element from an outer periphery thereof, in a second swaging position which is located in a lateral position of said second powder compact after said step d).

11. A gas sensor manufacturing apparatus, said apparatus including at least an element for obtaining an assembled body constituting said gas sensor by performing a predetermined processing on a semi-assembled body which is manufactured in advance, and said semi-assembled body comprising:
an annular-mounted assembly in which a plurality of annularly-mounted members each having a disc shape or cylindrical shape are annularly mounted around a sensor element with an elongated plate shape comprising a ceramic, the plurality of annularly-mounted members including at least a first ceramic powder compact located on one end side of said sensor element and a second ceramic powder compact located on an other end side of said sensor element opposite said one end side of said sensor element; and
a tubular body which is annularly mounted to an outer periphery of said annularly-mounted members and capable of engaging one end side of said annularly-mounted members therein, and
said element for obtaining said assembled body comprising:
a positioning member abutting to said one end side of said sensor element constituting said semi-assembled body for positioning said sensor element;

a first compression element applying a first force to said annularly-mounted members from said other end side of said sensor element which has been positioned by said positioning member and thereby performing a first compression of compressing said first powder compact and said second powder compact so as to fix said sensor element inside of said tubular body; and a second compression element applying, after said first compression, a second force which is larger than said first force to said annularly-mounted members from said other end side of said sensor element with said one end side of said sensor element not abutting to said positioning member and thereby performing a second compression of further compressing said first powder compact and said second powder compact so as to hermetically seal between spaces located on said one end side and said other end side of said sensor element is performed inside of said tubular body.

12. The gas sensor manufacturing apparatus according to claim 11, wherein a posture of said semi-assembled body in which a longitudinal direction of said sensor element extends in a vertical direction and said other end side is located upper side is defined as an assembly posture of said semi-assembled body, said positioning member abuts to said one end side of said sensor element from a lower side of said sensor element with said semi-assembled body being in said assembly posture, in said first compression, said first force is applied to an upper portion of said annularly-mounted members as a vertically downward force under a state that said semi-assembled body is in said assembly posture and said sensor element has been positioned with said positioning member, so that said first powder compact and said second powder compact are compressed, and said sensor element is fixed in a first position depending on a position of said positioning member by said compressed powder compact, and in said second compression, said second force is applied to said upper portion of said annularly-mounted members in said state where said semi-assembled body is in said assembly posture.

13. The gas sensor manufacturing apparatus according to claim 12, wherein said sensor element is displaced from said first position to a second position in a vertical direction through said second compression, and said positioning member is disposed so that said second position is located within a predetermined range which is determined in advance as a position of said sensor element in said assembled body.

14. The gas sensor manufacturing apparatus according to claim 13, wherein said positioning member is disposed so that said second position is located within said predetermined range which is determined based on a correlation between said first position and said second position of said sensor element, said correlation being specified in advance.

15. The gas sensor manufacturing apparatus according to claim 12, said element for obtaining said assembled body further comprising:

a first swaging element performing a first swaging for swaging said tubular body, in said state where said semi-assembled body is in said assembly posture, from an outer periphery thereof, in a first swaging position which is located above an uppermost portion of said annularly-mounted members whose said first powder compact and said second powder compact has been compressed by said second compression.

16. The gas sensor manufacturing apparatus according to claim 15, wherein said first compression element performs said first swaging with said second compression element keeping to apply said second force to said upper portion of said annularly-mounted members.

17. The gas senor manufacturing apparatus according to claim 15, said element for obtaining said assembled body further comprising:

a second swaging element performing a second swaging for swaging said tubular body, in said state where said semi-assembled body is in said assembly posture, from an outer periphery thereof, in a second swaging position which is located in a lateral position of said second powder compact after said first swaging.

* * * * *